US009193961B2

(12) United States Patent
Liebeton et al.

(10) Patent No.: US 9,193,961 B2
(45) Date of Patent: Nov. 24, 2015

(54) POLYNUCLEOTIDES ENCODING ENANTIOSELECTIVE CARBOXYLESTERASES AND METHODS OF MAKING SAME

(75) Inventors: Klaus Liebeton, Zwingenberg (DE); Jürgen Eck, Bensheim (DE); Uwe Bornscheuer, Greifswald (DE); Dominique Böttcher, Sponhlz (DE); Peter Langer, Rostock (DE); Esen Bellur, Adana (TR)

(73) Assignee: B.R.A.I.N. AG, Swingenberg (DE)

( * ) Notice: Subject to any disclaimer, the term of this patent is extended or adjusted under 35 U.S.C. 154(b) by 686 days.

(21) Appl. No.: 12/300,275

(22) PCT Filed: May 3, 2007

(86) PCT No.: PCT/EP2007/003919
§ 371 (c)(1),
(2), (4) Date: May 29, 2009

(87) PCT Pub. No.: WO2007/128496
PCT Pub. Date: Nov. 15, 2007

(65) Prior Publication Data
US 2009/0311745 A1 Dec. 17, 2009

(30) Foreign Application Priority Data
May 9, 2006 (EP) .................................. 06009545

(51) Int. Cl.
*A61K 38/00* (2006.01)
*C12N 9/18* (2006.01)

(52) U.S. Cl.
CPC ...................................... *C12N 9/18* (2013.01)

(58) Field of Classification Search
None
See application file for complete search history.

(56) References Cited

FOREIGN PATENT DOCUMENTS

WO         01/42436 A2     6/2001
WO     WO 2005/032496 A2   4/2005

OTHER PUBLICATIONS

Wells, Biochemistry, vol. 29, pp. 8509-8517, 1990.*
Seffernick et al. (J. Bacteriology, vol. 183, pp. 2405-2410, 2001).*
Bornscheuer, Uwe, T., Methods to Increase Enantioselectiveity of Lipases and Esterases, Chemical Biotechnology, 12:543-547 (2002).
Bornscheuer, Uwe, T., Microbial Carboxyl Esterases: Classification, Properties and Application in Biocatalysis, FEMS Microbiology Reviews, 26:73-81 (2002).
Choi, Gi-Sub, et al., Construction and Characterization of a Recombinant Esterase with High Activity and Enantioselectivity to (S)-Ketoprofen Ethyl Ester, Protein Expression & Purification, 29:85-93 (2003).
Database UniProt [Online] Sequence Version Archive, Sep. 5, 2006, "Probable Lactone Hydrolate." XP002450018 retreived from EBI accession No. UNIPROT:AOSDI7 Database accession No. QOSDI7.
Database EMBL [Online], Oct. 23, 2001, "Rhodococcus ruber strain SC1 cyclododecanone oxidation gene cluster, complete cds." XP002450019 retrieved from EBI accession No. EMBL:AY052630 Database accession No. AYO52630.
Henke, Erik, et al., A Molecular Mechanism of Enantiorecognition of Tertiary Alcohols by Carboxylesterases, ChemBioChem 4:485-493 (2003).
Kostichka, Kristy, et al., Cloning and Characterization of a Gene Cluster for Cyclododecanone Oxidation in *Rhodococcus ruber* SC1, Journal of Bacteriology, 183(21):6478-6486 (2001).
Krebsfanger, Niels, et al., Enantioselectivity of a Recombinant Esterase from *Pseudomonas fluorescens* towards alcohols and carboxylic acids, Journal of Biotechnology, 60:105-111 (1998).
Smeets, J.W.H., et al., Enzymatic Enantioselective Ester Hydrolysis by Carboxylesterase NP, Recl. Tray. Chim. Pays-Bas, 111:490-495 (1992).
Sousa, Helena, A., et al., Kinetic Study of the Enantioselective Hydrolysis of a Meso-Diester Using Pig Liver Esterase, J. Chem. Technol. Biotechnol., 75:707-714 (2000).
Bornscheuer, U.T., Methods to Increase Enantioselectivity of Lipases an Esterases, Current Opinion in Biotechnology, 2002, 13:543-547.
Bornscheuer, U.T., Microbial Carboxyl Esterases: Classification, Properties and Application in Biocatalysis, FEMS Microbiology Reviews, 2002, 26:73-81.
Choi, Gi-Sub et al., Construction and Characterization of a Recombinant esterase with High Activity and Enantioselectiveity to (S)-Ketoprofen Ethyl Ester, Protein Expression and Purification, 2003 29:85-93.
Henke, E., et al., A Molecular Mechanism of Enantiorecognition of Tertiary Alcohols by Carboxylesterases, ChemBioChem, 2003, 4:485-493.
Krebsfänger, N., et al., Enantioselectiveity of a Recombinant Esterase From *Pseudomonas Fluorescens* Towards Alcohols and Carboxylic Acids, Journal of Biotechnology, 1998, 60:105-111.
Smeets, J.W.H., et al., Enzymatic Enantioselective Ester hydrolysis by Carboxylesterase NP, Recueil des Travaux Chimiques des Pays-Bas, 1992, 111:490-495.
Sousa, H.A., et al., Kinetic Study of the Enantioselective Hydrolysis of a Meso-Diester Using Pig Liver Esterase, Journal of Chemical Technology and Biotechnology, 2000, 75:707-714.
EP Application No. 11002834.7, Partial European Search Report dated Sep. 21, 2011.

* cited by examiner

*Primary Examiner* — Hope Robinson
(74) *Attorney, Agent, or Firm* — Pillsbury Winthrop Shaw Pittmann LLP

(57) ABSTRACT

The present invention relates to a polynucleotide encoding an enzyme having carboxylesterase [E.C.3.1.1.1] activity.

18 Claims, 4 Drawing Sheets

Fig. 1 SEQ ID NO: 1 (Est1)

ATGCTGGCGCTGCATTCGAAGTTCGAGCCGCTGCGTGAGCTGTTCGACGCCAAGCTCGAATCG
GGCGACGACCTCGGCGCGTCGCTCGCGATCGACATCGATGGCGAGATGGTGGTCGACCTGTGG
GGCGGCTGGGCCGACGAGGCCAAGACCACGCCGTGGGGTGAGCACACGATCACCAACGTCTGG
TCGACGACCAAGACGATGACATCGCTGGCCGCGCTGATGCTCGTCGACCGCGGCGAGCTCGAC
CTCGACGCAACGGTCGCGAGCTACTGGCCCGAGTTCTCGGCCCGCGGCAAGCAAGGCGTGAAG
GTGCGCCATCTGCTGTCGCACATGTCGGGTGTCGCCGGCTGGGACCAGCCGGTGAAGATTGAA
GACGTGTACGACTGGGATAAGTCGACCGCGATGCTCGCCGCGCAGGCGCCGTGGTGGGAGCCC
GGCACCGCGTCGGGTTACCACGCGCTGAACTACGGCCACCTGATCGGCGAGGTGGTCCGCCGC
ATCACCGGCCAGCGCCTGGGCGCGTTCTTCGCCACCGAGATCGCACGGCCCTTGGGCGCGGAC
TTTCACATCGGGCTAGCGCCGAGCGAATTCCACCGCGTGTCGAACGTCGTTCCGCCGCCGCCA
TTGCCCATCGACCTGACGCAGCTCGACCCGAACGGCGCGATGTTCAAGACCTTCACCGGCCCC
GGCCCGCAGGCGGACGCGAGCTGGACCGAAGCATGGCGCCGTGCCGACATCGGCGGCGCGAAC
GGGCATGGCAATGCCCGTTCGGTGGCGCGCATCCAGTCGGCGGTGGCGTGTGGAGGCACGGTC
GGCGGCGTCAAGCTGCTGTCGCCGAAGACGATCGAGAAGATCTTCGAGGTGCAGAGCCACGCA
CCCGACCTGGTGCTCGGACTACCGCTGAAGATGGGCGTCGGTTATGGCTTGCCGATGCCGCAG
GTGCTGCCCTACATCCCCGACCGCAAGATCTGCTTCTGGGGCGGCTGGGGCGGCTCGATGGTG
ATCATCGACGTCGAGCGCCGCATGACGGTCGCCTACATGATGAACAAGATGGCACCCGGCATC
GTCGGCGGGCCCAACGCGGCGGCGCTGCTCGAGCGCGTCTACCAGATCGCCGACGCTTGA

Fig. 2 SEQ ID NO: 2 (Est1)

MLALHSKFEPLRELFDAKLESGDDLGASLAIDIDGEMVVDLWGGWADEAKTTPWGEHTITNVW
STTKTMTSLAALMLVDRGELDLDATVASYWPEFSARGKQGVKVRHLLSHMSGVAGWDQPVKIE
DVYDWDKSTAMLAAQAPWWEPGTASGYHALNYGHLIGEVVRRITGQRLGAFFATEIARPLGAD
FHIGLAPSEFHRVSNVVPPPPLPIDLTQLDPNGAMFKTFTGPGPQADASWTEAWRRADIGGAN
GHGNARSVARIQSAVACGGTVGGVKLLSPKTIEKIFEVQSHAPDLVLGLPLKMGVGYGLPMPQ
VLPYIPDRKICFWGGWGGSMVIIDVERRMTVAYMMNKMAPGIVGGPNAAALLERVYQIADA

Fig. 3 SEQ ID NO: 3 (Est5)

ATGACAACCTCCACACAAAACATCAGCGAGCTGCCTCTCTTACCTGGCCGTCTCGGTGATCCC
AGCAGAGTTTTGAAGACTGATCCACGCGCTGATCCGCGCTTGGTCGCCGCTTGCGCCCCCTTT
GCTCTAGACGTTGCTCCTCCACCCGTTCCGGTTACTGCAAACTCGCCCTTGGCGGACAAGCTT
GCCTACGCTGCAGCCAACGAGTCGGGCATGGAAGCCGTGTTTGCTGCTGTGTTCGCTGACCTC
TCTCCGATTACCAACGTGAAGCGGCGGACTGAAGTCATCAAGGGCGTGGATGAGAACGACATC
AGTCTCTATATCCATACGCCCCAGAACATGTCCGGCCCACTCCCTGCGTGTATCATGCACAC
GGCGGCGGTATGGTCCTGCTGACGGCCGCTGGTCCGACCTATGTGCGCTGGCGTGACGAGCTG
GCTGCCCTCGGCATGGTCGTGGTCGGCGTGGAATTTCGTAATGGCGCAGGCAAGCTAGGCAAT
CATCCATTTCCTGCGGGTCTCAACGACTGCATGAGTGGCCTGCAGTGGGTGTTTGACCACAAG
GCTGCCTTGGGAATCTCAAAGATTATCACATCTGGTGAATCTGGTGGTGGCAATCTTGCCTTG
GCTGTGTGTTTAAAAGCCAAAAAGGACAACCGCCTTGCTCAGATTGCTGGAGTCTACGCCCTG
TGCCCGTACATTTATGGCGCCTGGGCGCAGAAAAGCAAAGAGCTCCCGTCGCTGGTGGAAAAC
AACTGCTACTTGATCGACGTTCGCTCGATGGAAGTGCTGGCGAGCATCTATGACCCCGAGAAC
AAAAACGCCACCAATCCGCTGTGCTGGCCATACTGGGCCACGCGCGAGGATCTGCAAGGGTTG
CCCCCGCATGTTATCTCAGTCAACGAGTTAGACCCACTACGGGACGAGGGACTGAAATATTAT
CAGAAGCTCATGGCGGCTGGAGTGCGCGTGTACAGCCGGACCGTCAACGGCACGTGTCACGCT
GCTGACGTCCTGTTCCGCAAGGCGCTCCCGGAGGTGTACGCGGCCACCCTCCGCGATATCAAG
GGGTTCGCTGACTCGCTGTAG

Fig. 4 SEQ ID NO: 4 (Est5):

MTTSTQNISELPLLPGRLGDPSRVLKTDPRADPRLVAACAPFALDVAPPPVPVTANSPLADKL
AYAAANESGMEAVFAAVFADLSPITNVKRRTEVIKGVDENDISLYIHTPQNMSGPLPCVYHAH
GGGMVLLTAAGPTYVRWRDELAALGMVVVGVEFRNGAGKLGNHPFPAGLNDCMSGLQWVFDHK
AALGISKIITSGESGGGNLALAVCLKAKKDNRLAQIAGVYALCPYIYGAWAQKSKELPSLVEN
NCYLIDVRSMEVLASIYDPENKNATNPLCWPYWATREDLQGLPPHVISVNELDPLRDEGLKYY
QKLMAAGVRVYSRTVNGTCHAADVLFRKALPEVYAATLRDIKGFADSL

Fig. 5 SEQ ID NO: 5 (Est7)

ATGAGCAAGTTGCGGACAGCATTGATCTCCACCATCGGGCTCGCATGCGTACTGTGCGGCGTC
GCTGCCCAGGCGGACTCGGGCGCGCTCAAGCAGAAGGTCGACGCCGTGATCGACAAGGCGATC
GCGGAAGACCGCATCGTTGGCGCAGTCGTGCTCGTCGCACAGGACGGCCGACTCGTTTACGAG
CGGGCAGCCGGCCTGGCCGACAAGGAGTCCCGCAAACCGATGCAAATCGATGCGCTGTTCCGT
TTCTCCTCGGTATCGAAGCCGATCGTGACGGTCGCCGCGCTCGCGCTCGTCGATCGCAAGAAG
CTCTCGCTCGACGATCCCGTGACGAAGTGGCTGCCGGACTTCAAGCCGAAACTCGCCGACGGC
ACCTCGCCGACGATTACGGTTCGACAACTTCTGACGCACACCGCGGGCCTCGGCTACAAGTTC
GTGGAAAAGCCCGACGGGCCGTATCACAAAGCACAGATCTCCGACGGCTTCGACGACGTGAAG
ATCGACCTCGCTGAAGAAATGCGGCGCCTCTCGAACGTTCCGCTGCTCAACGCTCCGGCAAGC
CAATGGCGTTATTCGCTCTCGATCGACGTGCTGGGTGCAGTCATCGAGCGCGCGGCGGGCCAG
CCGCTCGGCACTGTCGTTGCGGAGCTCGTGACGAAACCGCTCGGGATGACCGGGACGTCGTTC
CGCGGTCGACCGCGCACAAGCCGATCGGGTCGCGATACCTTACTTCAACGCACCGTCGGGCAC
TGCACGCATGGCAGATCCGCAGAACGTTCCCTTCGGTACGGGCGCACTCGTGTACTCACCATC
GCGAGCCTTCGATTCGAAAGCGTACCCCGTCGGGCGGTGCCGGCATGA

Fig. 6 SEQ ID NO: 6 (Est7):

MSKLRTALISTIGLACVLCGVAAQADSGALKQKVDAVIDKAIAEDRIVGAVVLVAQDGRLVYE
RAAGLADKESRKPMQIDALFRFSSVSKPIVTVAALALVDRKKLSLDDPVTKWLPDFKPKLADG
TSPTITVRQLLTHTAGLGYKFVEKPDGPYHKAQISDGFDDVKIDLAEEMRRLSNVPLLNAPAS
QWRYSLSIDVLGAVIERAAGQPLGTVVAELVTKPLGMTGTSFRGRPRTSRSGRDTLLQRTVGH
CTHGRSAERSLRYGRTRVLTIASLRFESVPRRAVPA

Fig. 7 SEQ ID NO: 7 (Est8):

ATGGCGAGTCCGCAACTACAGATGGCGCTTGATGGGTTCAAGATGATGGGAGAGAAGATGGCG
CAGGCCGGTGGGGACGTGAAGGCAATGCGTGCCGTTATGGAAGAGATGGCCACCTTTCCCTCG
GCAGGAGAAACGAAGTGCACTCCAGTGAATGCGGGTGGCGTCCCAGCTGAGTGGATTGCTGCT
CCGGGGGCAGCGGACGACCGCGTGATCTTGTATCTCCATGGTGGCGGCTACGTGATGGGCTCT
ATTACCACGCACCGTGAGACGATCGCACGCTTATCGAAAGCCTCAGGAGCGCGAGCGCTGGCG
CTCGATTATCGCTTAGCTCCGGAGTATCCATTTCCCGCCGCCGTGGATGACGCAACGGCAGCC
TATCGCTGGTTGTTATCACAAGATATCAAGCCGTCTCGTATTGTCGTGGCTGGAGACTCTGCC
GGAGGCGGGCTCGTTCTGGCCACGCTGGTGGCGCTGCGCGATGCGAAAGTCCCTCTGCCCGCG
GCAGGAGTGTGCATTTCACCATGGGCGGATATGGAAGGGACCGGCGCATCCATGACAACCAGA
GCGAAGGCTGATCCGGTGGTGCAAAAAGAGATGCTCGTCAACATGGGAAAGACGTATCTCGGT
GGCAAAGACGCAAAATCACCGCTCGCGGCTCCACTTCATGCTGATTTCCGAGGACTGCCCCCG
CTGTTCATTCAGGTTGGCGACGCCGAGACGTTGCTTGATGACTCCACCCGTGTTGCGGAAAAG
GCGAAGATGGCTGGGGTCAAGGTGGATCTCGAGATCTGGCCGGAGATGCCACACGTATGGCAT
CTATTTGCTCCTTTCCTACCGGAAGGGCAACAAGCCATCGATAAGATCGGCCAGTACGTAAAG
CAGCGAACTGCTTAG

Fig. 8 SEQ ID NO: 8 (Est8):

MASPQLQMALDGFKMMGEKMAQAGGDVKAMRAVMEEMATFPSAGETKCTPVNAGGVPAEWIAA
PGAADDRVILYLHGGGYVMGSITTHRETIARLSKASGARALALDYRLAPEYPFPAAVDDATAA
YRWLLSQDIKPSRIVVAGDSAGGGLVLATLVALRDAKVPLPAAGVCISPWADMEGTGASMTTR
AKADPVVQKEMLVNMGKTYLGGKDAKSPLAAPLHADFRGLPPLFIQVGDAETLLDDSTRVAEK
AKMAGVKVDLEIWPEMPHVWHLFAPFLPEGQQAIDKIGQYVKQRTA

Fig. 9 SEQ ID NO: 9 (Est56):

ATGCCACTCGATCAACCCACCGCCGCGTTCCTCGACTTCCTCCGCTCGTCCGGCGGCAAACCG
CTGTATGAGCTGCCCCTTGCCGAGGCGCGCGCCGCCATGGCAATGGGTTCGCAGCTTGGCGCG
CCCCCGGCCGACGTGGGGCGCATTGTCGATCGCTCCATCGACGTGCCGGGCGGCGCCGTTGCC
TTGCGCATCTACACGCCCGCGACGACCAAGGCCGGCGGGCTGCTGCCCGCGATCCTGCAATAC
CACGGCGGCGGATTCGTGCTCGGCAACCTGGACACCCACGAGTCGATCGCGCGGTTTTACTGC
GCGCACGCCGGCGCCGTGGTGATCAGCGTCGACTACCGCCTGGCACCGGAGCATCGCTTCCCC
ACGCAGGTGGAGGACTCGTTCGCGGCGCTGACGTGGGTCAGCGAACATGCGAGCGAGCTCGGG
GTGGATCCGGCGCGCGTGGCGGTTGCGGGCGACAGCGCGGGAGGCAATCTGGCGACCGTGATG
TGCCTGCTGGCGAAGGCGCGGGGCGGGCCTCGCATCGCGTGCCAGGCACTGCTCTATCCCGTG
GCCGACTTCAGGCCCGAGCAGGTGTACGCGTCGCACGCGCAGTTCGGTGACGGCAGCTATTTC
CTGTCCTCGAAGGACATGGACTGGTTCCGCGCCTCGTATTTCACCGACGTCGCATCCCAGGCA
GCCGAGCCAACCGCGTCGCCGATGGCCACAACAGACCTCAGCGGTTTACCTCCGGCACTGGTC
ACGACGGCCGGGTGCGATCCGCTCCTCGACGAGGGGCGGGCCTACGCCGATCGCCTGAAAGCC
GCTGGCGTGCCCGTGGACTATCGCTGCTTCGAGACGACCATCCACGCGTGCGCCTCGTTTGCG
GGAACGATTCCGGCGGGGCTCGACATGCTGGGCTTCGTGGCGGACTGGCTGGCGGCGCACACG
AAATAG

Fig. 10    SEQ ID NO: 10 (Est56):

MPLDQPTAAFLDFLRSSGGKPLYELPLAEARAAMAMGSQLGAPPADVGRIVDRSIDVPGGAVA
LRIYTPATTKAGGLLPAILQYHGGGFVLGNLDTHESIARFYCAHAGAVVISVDYRLAPEHRFP
TQVEDSFAALTWVSEHASELGVDPARVAVAGDSAGGNLATVMCLLAKARGGPRIACQALLYPV
ADFRPEQVYASHAQFGDGSYFLSSKDMDWFRASYFTDVASQAAEPTASPMATTDLSGLPPALV
TTAGCDPLLDEGRAYADRLKAAGVPVDYRCFETTIHACASFAGTIPAGLDMLGFVADWLAAHT
K

Fig. 11    SEQ ID NO: 11 (Est63):

ATGCCATTACATCCCCAAGTCAAAGCCGTTCTCGAACTCATGGAAAAAGCCGGACCGCCGATG
CACCATCTTTCACCGCAACACGCGCGTGAACAGATTCTCGCCATGCGTGCCACCAAGGGCGAA
CCTGAGCCCGTAGGCAAGGTAGAAGATCGGACTATCAAAGATTCAGCAGGAGATATTCCGGTT
CGGATTTACACCCCGAATGGTCGTGGCCCATTTCCTTTACTGGTGTATTTTCACGGCGGAGGG
TGGGTTGTCGGCAGTGTCGAAACGGTTGACGCTTCATGTCGTGCGCTCACGAACCTCGCAAAC
TGCGTTACGGTCTCAGTTGAGTATCGACTCGCGCCTGAACACAAATTCCCGGCACCGGTGGAC
GATTGCTATGCTGCAACCCGATGGACAGCCTTGAATGCTGCTTCCTTCCACGGGGACCCGGCA
CGGATTGCTGTGGGTGGTGAAAGTGCAGGGGCAAACCTTGCCGCTGCGGTGGCATTGATGGCG
CAAGAGCGCGGGGCTCCATCTCTCGTTCATCAGTTGTTGTATATCCGGTGACGAATTACGCT
TCTGATCTGCCGTCTCACAAAGCGAATGCCACAGGGTATTTCTTGACGACGGAGATGATGCGG
TGGTTTTGGAACCATTACCTGCGGAACGAGACCGATGGAGAAAATCCCCTCGCTTCACCACTG
CGTGCCAAGCGGTTGCAAGGGCTTGCTCCAGCGACGATCTACACCGCAGAGTTTGACCCGCTA
CGAGATGAAGGTGCGGCATACGCGACCAAACTCCGTGAAGCGGGAATCGCTGTCGAGTACACG
TGCTACGAGGGTTTGATTCACGGTTTCATGGGAATGGCGAAAGCTGTCGAACCGGCGAAGAAG
GCACTGGAAGATGCCGGTGCTGCGTTGCGGAAGGCGTTGGCGTAG

Fig. 12    SEQ ID NO:12 (Est63):

MPLHPQVKAVLELMEKAGPPMHHLSPQHAREQILAMRATKGEPEPVGKVEDRTIKDSAGDIPV
RIYTPNGRGPFPLLVYFHGGGWVVGSVETVDASCRALTNLANCVTVSVEYRLAPEHKFPAPVD
DCYAATRWTALNAASFHGDPARIAVGGESAGANLAAAVALMAQERGAPSLVHQLLLYPVTNYA
SDLPSHKANATGYFLTTEMMRWFWNHYLRNETDGENPLASPLRAKRLQGLAPATIYTAEFDPL
RDEGAAYATKLREAGIAVEYTCYEGLIHGFMGMAKAVEPAKKALEDAGAALRKALA

SEQUENCE LISTING

```
<160> NUMBER OF SEQ ID NOS: 15

<210> SEQ ID NO 1
<211> LENGTH: 1131
<212> TYPE: DNA
<213> ORGANISM: unknown
<220> FEATURE:
<221> NAME/KEY: source
<223> OTHER INFORMATION: /note="Description of unknown sequence:
      metagenomic expression library"

<400> SEQUENCE: 1
atgctggcgc tgcattcgaa gttcgagccg ctgcgtgagc tgttcgacgc caagctcgaa      60
tcgggcgacg acctcggcgc gtcgctcgcg atcgacatcg atggcgagat ggtggtcgac     120
ctgtggggcg gctgggccga cgaggccaag accacgccgt ggggtgagca cacgatcacc     180
aacgtctggt cgacgaccaa gacgatgaca tcgctggccg cgctgatgct cgtcgaccgc     240
ggcgagctcg acctcgacgc aacggtcgcg agctactggc ccgagttctc ggcccgcggc     300
aagcaaggcg tgaaggtgcg ccatctgctg tcgcacatgt cgggtgtcgc cggctgggac     360
cagccggtga agattgaaga cgtgtacgac tgggataagt cgaccgcgat gctcgccgcg     420
caggcgccgt ggtgggagcc cggcaccgcg tcgggttacc acgcgctgaa ctacggccac     480
ctgatcggcg aggtggtccg ccgcatcacc ggccagcgcc tgggcgcgtt cttcgccacc     540
gagatcgcac ggcccttggg cgcggacttt cacatcgggc tagcgccgag cgaattccac     600
cgcgtgtcga acgtcgttcc gccgccgcca ttgcccatcg acctgacgca gctcgacccg     660 aacgcgcga tgttcaagac cttcaccggc cccgcccgc aggcggacgc gagctggacc     720
gaagcatggc gccgtgccga catcggcggc gcgaacgggc atggcaatgc ccgttcggtg     780
gcgcgcatcc agtcggcggt ggcgtgtgga ggcacggtcg gcggcgtcaa gctgctgtcg     840
ccgaagacga tcgagaagat cttcgaggtg cagagccacg caccgaccct ggtgctcgga     900
ctaccgctga gatgggcgt cggttatggc ttgccgatgc gcaggtgct gccctacatc     960 cccgaccgca agatctgctt ctggggcggc tggggcggct cgatggtgat catcgacgtc    1020
gagcgccgca tgacggtcgc ctacatgatg aacaagatgg caccggcat cgtcggcggg    1080 cccaacgcgg cggcgctgct cgagcgcgtc taccagatcg ccgacgcttg a             1131

<210> SEQ ID NO 2
<211> LENGTH: 376
<212> TYPE: PRT
<213> ORGANISM: unknown
<220> FEATURE:
<221> NAME/KEY: source
<223> OTHER INFORMATION: /note="Description of unknown sequence:
      metagenomic expression library"
```

```
<400> SEQUENCE: 2

Met Leu Ala Leu His Ser Lys Phe Glu Pro Leu Arg Glu Leu Phe Asp
 1               5                  10                  15

Ala Lys Leu Glu Ser Gly Asp Leu Gly Ala Ser Leu Ala Ile Asp
             20                  25                  30

Ile Asp Gly Glu Met Val Val Asp Leu Trp Gly Trp Ala Asp Glu
         35                  40                  45

Ala Lys Thr Thr Pro Trp Gly Glu His Thr Ile Thr Asn Val Trp Ser
 50                  55                  60

Thr Thr Lys Thr Met Thr Ser Leu Ala Ala Leu Met Leu Val Asp Arg
 65                  70                  75                  80

Gly Glu Leu Asp Leu Asp Ala Thr Val Ala Ser Tyr Trp Pro Glu Phe
                 85                  90                  95

Ser Ala Arg Gly Lys Gln Gly Val Lys Val Arg His Leu Leu Ser His
             100                 105                 110

Met Ser Gly Val Ala Gly Trp Asp Gln Pro Val Lys Ile Glu Asp Val
         115                 120                 125

Tyr Asp Trp Asp Lys Ser Thr Ala Met Leu Ala Ala Gln Ala Pro Trp
130                 135                 140

Trp Glu Pro Gly Thr Ala Ser Gly Tyr His Ala Leu Asn Tyr Gly His
145                 150                 155                 160

Leu Ile Gly Glu Val Val Arg Arg Ile Thr Gly Gln Arg Leu Gly Ala
                165                 170                 175

Phe Phe Ala Thr Glu Ile Ala Arg Pro Leu Gly Ala Asp Phe His Ile
            180                 185                 190

Gly Leu Ala Pro Ser Glu Phe His Arg Val Ser Asn Val Val Pro Pro
        195                 200                 205

Pro Pro Leu Pro Ile Asp Leu Thr Gln Leu Asp Pro Asn Gly Ala Met
210                 215                 220

Phe Lys Thr Phe Thr Gly Pro Gly Pro Gln Ala Asp Ala Ser Trp Thr
225                 230                 235                 240

Glu Ala Trp Arg Arg Ala Asp Ile Gly Gly Ala Asn Gly His Gly Asn
                245                 250                 255

Ala Arg Ser Val Ala Arg Ile Gln Ser Ala Val Ala Cys Gly Gly Thr
            260                 265                 270

Val Gly Gly Val Lys Leu Leu Ser Pro Lys Thr Ile Glu Lys Ile Phe
        275                 280                 285

Glu Val Gln Ser His Ala Pro Asp Leu Val Leu Gly Leu Pro Leu Lys
290                 295                 300

Met Gly Val Gly Tyr Gly Leu Pro Met Pro Gln Val Leu Pro Tyr Ile
305                 310                 315                 320

Pro Asp Arg Lys Ile Cys Phe Trp Gly Trp Gly Gly Ser Met Val
                325                 330                 335

Ile Ile Asp Val Glu Arg Arg Met Thr Val Ala Tyr Met Met Asn Lys
            340                 345                 350

Met Ala Pro Gly Ile Val Gly Gly Pro Asn Ala Ala Ala Leu Leu Glu
        355                 360                 365

Arg Val Tyr Gln Ile Ala Asp Ala
    370                 375

<210> SEQ ID NO 3
<211> LENGTH: 1092
<212> TYPE: DNA
<213> ORGANISM: unknown
```

```
<220> FEATURE:
<221> NAME/KEY: source
<223> OTHER INFORMATION: /note="Description of unknown sequence:
      metagenomic expression library"

<400> SEQUENCE: 3
atgacaacct ccacacaaaa catcagcgag ctgcctctct tacctggccg tctcggtgat      60
cccagcagag ttttgaagac tgatccacgc gctgatccgc gcttggtcgc cgcttgcgcc    120
ccctttgctc tagacgttgc tcctccaccc gttccggtta ctgcaaactc gcccttggcg    180
gacaagcttg cctacgctgc agccaacgag tcgggcatgg aagccgtgtt tgctgctgtg    240
ttcgctgacc tctctccgat taccaacgtg aagcggcgga ctgaagtcat caagggcgtg    300
gatgagaacg acatcagtct ctatatccat acgccccaga acatgtccgg cccactcccc    360
tgcgtgtatc atgcacacgg cggcggtatg gtcctgctga cggccgctgg tccgacctat    420
gtgcgctggc gtgacgagct ggctgccctc ggcatggtcg tggtcggcgt ggaatttcgt    480
aatggcgcag gcaagctagg caatcatcca tttcctgcgg gtctcaacga ctgcatgagt    540
ggcctgcagt gggtgtttga ccacaaggct gccttgggaa tctcaaagat tatcacatct    600
ggtgaatctg gtggtggcaa tcttgccttg gctgtgtgtt taaaagccaa aaaggacaac    660
cgccttgctc agattgctgg agtctacgcc ctgtgcccgt acatttatgg cgcctgggcg    720
cagaaaagca aagagctccc gtcgctggtg gaaaacaact gctacttgat cgacgttcgc    780
tcgatggaag tgctggcgag catctatgac cccgagaaca aaaacgccac caatccgctg    840
tgctggccat actgggccac gcgcgaggat ctgcaagggt tgcccccgca tgttatctca    900
gtcaacgagt tagacccact acgggacgag ggactgaaat attatcagaa gctcatggcg    960
gctggagtgc gcgtgtacag ccggaccgtc aacggcacgt gtcacgctgc tgacgtcctg   1020
ttccgcaagg cgctcccgga ggtgtacgcg gccaccctcc gcgatatcaa ggggttcgct   1080
gactcgctgt ag                                                        1092

<210> SEQ ID NO 4
<211> LENGTH: 363
<212> TYPE: PRT
<213> ORGANISM: unknown
<220> FEATURE:
<221> NAME/KEY: source
<223> OTHER INFORMATION: /note="Description of unknown sequence:
      metagenomic expression library"

<400> SEQUENCE: 4

Met Thr Thr Ser Thr Gln Asn Ile Ser Glu Leu Pro Leu Pro Gly
1               5                   10                  15

Arg Leu Gly Asp Pro Ser Arg Val Leu Lys Thr Asp Pro Arg Ala Asp
                20                  25                  30

Pro Arg Leu Val Ala Ala Cys Ala Pro Phe Ala Leu Asp Val Ala Pro
            35                  40                  45

Pro Pro Val Pro Val Thr Ala Asn Ser Pro Leu Ala Asp Lys Leu Ala
        50                  55                  60

Tyr Ala Ala Ala Asn Glu Ser Gly Met Glu Ala Val Phe Ala Ala Val
65                  70                  75                  80

Phe Ala Asp Leu Ser Pro Ile Thr Asn Val Lys Arg Arg Thr Glu Val
                85                  90                  95

Ile Lys Gly Val Asp Glu Asn Asp Ile Ser Leu Tyr Ile His Thr Pro
            100                 105                 110

Gln Asn Met Ser Gly Pro Leu Pro Cys Val Tyr His Ala His Gly Gly
```

```
            115                 120                 125
Gly Met Val Leu Leu Thr Ala Ala Gly Pro Thr Tyr Val Arg Trp Arg
    130                 135                 140

Asp Glu Leu Ala Ala Leu Gly Met Val Val Gly Val Glu Phe Arg
145                 150                 155                 160

Asn Gly Ala Gly Lys Leu Gly Asn His Pro Phe Pro Ala Gly Leu Asn
                165                 170                 175

Asp Cys Met Ser Gly Leu Gln Trp Val Phe Asp His Lys Ala Ala Leu
            180                 185                 190

Gly Ile Ser Lys Ile Ile Thr Ser Gly Glu Ser Gly Gly Gly Asn Leu
        195                 200                 205

Ala Leu Ala Val Cys Leu Lys Ala Lys Asp Asn Arg Leu Ala Gln
    210                 215                 220

Ile Ala Gly Val Tyr Ala Leu Cys Pro Tyr Ile Tyr Gly Ala Trp Ala
225                 230                 235                 240

Gln Lys Ser Lys Glu Leu Pro Ser Leu Val Glu Asn Asn Cys Tyr Leu
                245                 250                 255

Ile Asp Val Arg Ser Met Glu Val Leu Ala Ser Ile Tyr Asp Pro Glu
            260                 265                 270

Asn Lys Asn Ala Thr Asn Pro Leu Cys Trp Pro Tyr Trp Ala Thr Arg
        275                 280                 285

Glu Asp Leu Gln Gly Leu Pro Pro His Val Ile Ser Val Asn Glu Leu
    290                 295                 300

Asp Pro Leu Arg Asp Glu Gly Leu Lys Tyr Tyr Gln Lys Leu Met Ala
305                 310                 315                 320

Ala Gly Val Arg Val Tyr Ser Arg Thr Val Asn Gly Thr Cys His Ala
                325                 330                 335

Ala Asp Val Leu Phe Arg Lys Ala Leu Pro Glu Val Tyr Ala Ala Thr
            340                 345                 350

Leu Arg Asp Ile Lys Gly Phe Ala Asp Ser Leu
        355                 360

<210> SEQ ID NO 5
<211> LENGTH: 867
<212> TYPE: DNA
<213> ORGANISM: unknown
<220> FEATURE:
<221> NAME/KEY: source
<223> OTHER INFORMATION: /note="Description of unknown sequence:
      metagenomic expression library"

<400> SEQUENCE: 5
atgagcaagt tgcggacagc attgatctcc accatcgggc tcgcatgcgt actgtgcggc      60
gtcgctgccc aggcggactc gggcgcgctc aagcagaagg tcgacgccgt gatcgacaag     120
gcgatcgcgg aagaccgcat cgttggcgca gtcgtgctcg tcgcacagga cggccgactc     180
gtttacgagc gggcagccgg cctggccgac aaggagtccc gcaaaccgat gcaaatcgat     240
gcgctgttcc gtttctcctc ggtatcgaag ccgatcgtga cggtcgccgc gctcgcgctc     300
gtcgatcgca agaagctctc gctcgacgat cccgtgacga agtggctgcc ggacttcaag     360
ccgaaactcg ccgacggcac ctcgccgacg attacggttc gacaacttct gacgcacacc     420
gcgggcctcg gctacaagtt cgtggaaaag cccgacgggc gtatcacaa agcacagatc      480 tccgacggct cgacgacgt gaagatcgac ctcgctgaag aaatgcggcg cctctcgaac      540
gttccgctgc tcaacgctcc ggcaagccaa tggcgttatt cgctctcgat cgacgtgctg     600
```

```
ggtgcagtca tcgagcgcgc ggcgggccag ccgctcggca ctgtcgttgc ggagctcgtg    660
acgaaaccgc tcgggatgac cgggacgtcg ttccgcggtc gaccgcgcac aagccgatcg    720
ggtcgcgata ccttacttca acgcaccgtc gggcactgca cgcatggcag atccgcagaa    780
cgttcccttc ggtacgggcg cactcgtgta ctcaccatcg cgagccttcg attcgaaagc    840
gtaccccgtc gggcggtgcc ggcatga                                       867
```

<210> SEQ ID NO 6
<211> LENGTH: 288
<212> TYPE: PRT
<213> ORGANISM: unknown
<220> FEATURE:
<221> NAME/KEY: source
<223> OTHER INFORMATION: /note="Description of unknown sequence: metagenomic expression library"

<400> SEQUENCE: 6

```
Met Ser Lys Leu Arg Thr Ala Leu Ile Ser Thr Ile Gly Leu Ala Cys
 1               5                  10                  15

Val Leu Cys Gly Val Ala Ala Gln Ala Asp Ser Gly Ala Leu Lys Gln
                20                  25                  30

Lys Val Asp Ala Val Ile Asp Lys Ala Ile Ala Glu Asp Arg Ile Val
            35                  40                  45

Gly Ala Val Val Leu Val Ala Gln Asp Gly Arg Leu Val Tyr Glu Arg
        50                  55                  60

Ala Ala Gly Leu Ala Asp Lys Glu Ser Arg Lys Pro Met Gln Ile Asp
 65                  70                  75                  80

Ala Leu Phe Arg Phe Ser Val Ser Lys Pro Ile Val Thr Val Ala
                 85                  90                  95

Ala Leu Ala Leu Val Asp Arg Lys Lys Leu Ser Leu Asp Pro Val
            100                 105                 110

Thr Lys Trp Leu Pro Asp Phe Lys Pro Lys Leu Ala Asp Gly Thr Ser
                115                 120                 125

Pro Thr Ile Thr Val Arg Gln Leu Leu Thr His Thr Ala Gly Leu Gly
        130                 135                 140

Tyr Lys Phe Val Glu Lys Pro Asp Gly Pro Tyr His Lys Ala Gln Ile
145                 150                 155                 160

Ser Asp Gly Phe Asp Asp Val Lys Ile Asp Leu Ala Glu Glu Met Arg
                165                 170                 175

Arg Leu Ser Asn Val Pro Leu Leu Asn Ala Pro Ala Ser Gln Trp Arg
            180                 185                 190

Tyr Ser Leu Ser Ile Asp Val Leu Gly Ala Val Ile Glu Arg Ala Ala
        195                 200                 205

Gly Gln Pro Leu Gly Thr Val Val Ala Glu Leu Val Thr Lys Pro Leu
    210                 215                 220

Gly Met Thr Gly Thr Ser Phe Arg Gly Arg Pro Arg Thr Ser Arg Ser
225                 230                 235                 240

Gly Arg Asp Thr Leu Leu Gln Arg Thr Val Gly His Cys Thr His Gly
                245                 250                 255

Arg Ser Ala Glu Arg Ser Leu Arg Tyr Gly Arg Thr Arg Val Leu Thr
            260                 265                 270

Ile Ala Ser Leu Arg Phe Glu Ser Val Pro Arg Arg Ala Val Pro Ala
        275                 280                 285
```

<210> SEQ ID NO 7
<211> LENGTH: 897

-continued

```
<212> TYPE: DNA
<213> ORGANISM: unknown
<220> FEATURE:
<221> NAME/KEY: source
<223> OTHER INFORMATION: /note="Description of unknown sequence:
      metagenomic expression library"

<400> SEQUENCE: 7
atggcgagtc cgcaactaca gatggcgctt gatgggttca agatgatggg agagaagatg      60
gcgcaggccg gtggggacgt gaaggcaatg cgtgccgtta tggaagagat ggccacctt     120 ccctcggcag agaaacgaa gtgcactcca gtgaatgcgg gtggcgtccc agctgagtgg     180
attgctgctc cggggcagc ggacgaccgc gtgatcttgt atctccatgg tggcggctac     240
gtgatgggct ctattaccac gcaccgtgag acgatcgcac gcttatcgaa agcctcagga     300
gcgcgagcgc tggcgctcga ttatcgctta gctccggagt atccatttcc cgccgccgtg     360
gatgacgcaa cggcagccta tcgctggttg ttatcacaag atatcaagcc gtctcgtatt     420
gtcgtggctg gagactctgc cggaggcggg ctcgttctgg ccacgctggt ggcgctgcgc     480
gatgcgaaag tccctctgcc cgcggcagga gtgtgcattt caccatgggc ggatatggaa     540
gggaccggcg catccatgac aaccagagcg aaggctgatc cggtggtgca aaaagagatg     600
ctcgtcaaca tgggaaagac gtatctcggt ggcaaagacg caaaatcacc gctcgcggct     660
ccacttcatg ctgatttccg aggactgccc ccgctgttca ttcaggttgg cgacgccgag     720
acgttgcttg atgactccac ccgtgttgcg gaaaaggcga gatggctgg ggtcaaggtg     780 gatctcgaga tctggccgga gatgccacac gtatggcatc tatttgctcc tttcctaccg     840
gaagggcaac aagccatcga taagatcggc cagtacgtaa agcagcgaac tgcttag      897

<210> SEQ ID NO 8
<211> LENGTH: 298
<212> TYPE: PRT
<213> ORGANISM: unknown
<220> FEATURE:
<221> NAME/KEY: source
<223> OTHER INFORMATION: /note="Description of unknown sequence:
      metagenomic expression library"

<400> SEQUENCE: 8

Met Ala Ser Pro Gln Leu Gln Met Ala Leu Asp Gly Phe Lys Met Met
1               5                  10                  15

Gly Glu Lys Met Ala Gln Ala Gly Gly Asp Val Lys Ala Met Arg Ala
            20                  25                  30

Val Met Glu Glu Met Ala Thr Phe Pro Ser Ala Gly Glu Thr Lys Cys
        35                  40                  45

Thr Pro Val Asn Ala Gly Gly Val Pro Ala Glu Trp Ile Ala Ala Pro
    50                  55                  60

Gly Ala Ala Asp Asp Arg Val Ile Leu Tyr Leu His Gly Gly Gly Tyr
65                  70                  75                  80

Val Met Gly Ser Ile Thr Thr His Arg Glu Thr Ile Ala Arg Leu Ser
                85                  90                  95

Lys Ala Ser Gly Ala Arg Ala Leu Ala Leu Asp Tyr Arg Leu Ala Pro
            100                 105                 110

Glu Tyr Pro Phe Pro Ala Ala Val Asp Asp Ala Thr Ala Ala Tyr Arg
        115                 120                 125

Trp Leu Leu Ser Gln Asp Ile Lys Pro Ser Arg Ile Val Val Ala Gly
    130                 135                 140

Asp Ser Ala Gly Gly Gly Leu Val Leu Ala Thr Leu Val Ala Leu Arg
```

```
            145                 150                 155                 160
Asp Ala Lys Val Pro Leu Pro Ala Ala Gly Val Cys Ile Ser Pro Trp
                165                 170                 175

Ala Asp Met Glu Gly Thr Gly Ala Ser Met Thr Thr Arg Ala Lys Ala
                180                 185                 190

Asp Pro Val Val Gln Lys Glu Met Leu Val Asn Met Gly Lys Thr Tyr
                195                 200                 205

Leu Gly Gly Lys Asp Ala Lys Ser Pro Leu Ala Ala Pro Leu His Ala
        210                 215                 220

Asp Phe Arg Gly Leu Pro Pro Leu Phe Ile Gln Val Gly Asp Ala Glu
225                 230                 235                 240

Thr Leu Leu Asp Asp Ser Thr Arg Val Ala Glu Lys Ala Lys Met Ala
                245                 250                 255

Gly Val Lys Val Asp Leu Glu Ile Trp Pro Glu Met Pro His Val Trp
                260                 265                 270

His Leu Phe Ala Pro Phe Leu Pro Glu Gly Gln Gln Ala Ile Asp Lys
                275                 280                 285

Ile Gly Gln Tyr Val Lys Gln Arg Thr Ala
        290                 295

<210> SEQ ID NO 9
<211> LENGTH: 951
<212> TYPE: DNA
<213> ORGANISM: unknown
<220> FEATURE:
<221> NAME/KEY: source
<223> OTHER INFORMATION: /note="Description of unknown sequence:
      metagenomic expression library"

<400> SEQUENCE: 9
atgccactcg atcaacccac cgccgcgttc ctcgacttcc tccgctcgtc cggcggcaaa      60
ccgctgtatg agctgcccct tgccgaggcg cgcgccgcca tggcaatggg ttcgcagctt     120
ggcgcgcccc cggccgacgt gggcgcatt gtcgatcgct ccatcgacgt gccgggcggc     180
gccgttgcct tgcgcatcta cacgcccgcg acgaccaagg ccggcgggct gctgcccgcg     240
atcctgcaat accacggcgg cggattcgtg ctcggcaacc tggacaccca cgagtcgatc     300
gcgcggtttt actgcgcgca cgccggcgcc gtggtgatca cgtcgactca ccgcctggca     360
ccggagcatc gcttccccac gcaggtggag gactcgttcg cggcgctgac gtgggtcagc     420
gaacatgcga gcgagctcgg ggtggatccg gcgcgcgtgg cggttgcggg cgacagcgcg     480
ggaggcaatc tggcgaccgt gatgtgcctg ctggcgaagg cgcggggcgg gcctcgcatc     540
gcgtgccagg cactgctcta tcccgtggcc gacttcaggc ccgagcaggt gtacgcgtcg     600
cacgcgcagt tcggtgacgg cagctatttc ctgtcctcga aggacatgga ctggttccgc     660
gcctcgtatt tcaccgacgt cgcatcccag gcagccgagc caaccgcgtc gccgatggcc     720
acaacagacc tcagcggttt acctccggca ctggtcacga cggccgggtg cgatccgctc     780
ctcgacgagg ggcgggccta cgccgatcgc ctgaaagccg ctggcgtgcc cgtggactat     840
cgctgcttcg agacgaccat ccacgcgtgc gcctcgtttg cgggaacgat tccggcgggg     900
ctcgacatgc tgggcttcgt ggcggactgg ctggcggcgc acacgaaata g             951

<210> SEQ ID NO 10
<211> LENGTH: 316
<212> TYPE: PRT
<213> ORGANISM: unknown
<220> FEATURE:
```

-continued

<221> NAME/KEY: source
<223> OTHER INFORMATION: /note="Description of unknown sequence:
      metagenomic expression library"

<400> SEQUENCE: 10

| Met | Pro | Leu | Asp | Gln | Pro | Thr | Ala | Ala | Phe | Leu | Asp | Phe | Leu | Arg | Ser |
|---|---|---|---|---|---|---|---|---|---|---|---|---|---|---|---|
| 1 |   |   |   | 5 |   |   |   |   | 10 |   |   |   |   | 15 |   |

| Ser | Gly | Gly | Lys | Pro | Leu | Tyr | Glu | Leu | Pro | Leu | Ala | Glu | Ala | Arg | Ala |
|---|---|---|---|---|---|---|---|---|---|---|---|---|---|---|---|
|   |   |   | 20 |   |   |   |   | 25 |   |   |   |   | 30 |   |   |

| Ala | Met | Ala | Met | Gly | Ser | Gln | Leu | Gly | Ala | Pro | Pro | Ala | Asp | Val | Gly |
|---|---|---|---|---|---|---|---|---|---|---|---|---|---|---|---|
|   |   | 35 |   |   |   |   | 40 |   |   |   |   | 45 |   |   |   |

| Arg | Ile | Val | Asp | Arg | Ser | Ile | Asp | Val | Pro | Gly | Gly | Ala | Val | Ala | Leu |
|---|---|---|---|---|---|---|---|---|---|---|---|---|---|---|---|
| 50 |   |   |   |   | 55 |   |   |   |   | 60 |   |   |   |   |   |

| Arg | Ile | Tyr | Thr | Pro | Ala | Thr | Thr | Lys | Ala | Gly | Gly | Leu | Leu | Pro | Ala |
|---|---|---|---|---|---|---|---|---|---|---|---|---|---|---|---|
| 65 |   |   |   | 70 |   |   |   |   | 75 |   |   |   |   | 80 |   |

| Ile | Leu | Gln | Tyr | His | Gly | Gly | Phe | Val | Leu | Gly | Asn | Leu | Asp | Thr |
|---|---|---|---|---|---|---|---|---|---|---|---|---|---|---|
|   |   |   |   | 85 |   |   |   | 90 |   |   |   |   | 95 |   |

| His | Glu | Ser | Ile | Ala | Arg | Phe | Tyr | Cys | Ala | His | Ala | Gly | Ala | Val | Val |
|---|---|---|---|---|---|---|---|---|---|---|---|---|---|---|---|
|   |   |   | 100 |   |   |   |   | 105 |   |   |   |   | 110 |   |   |

| Ile | Ser | Val | Asp | Tyr | Arg | Leu | Ala | Pro | Glu | His | Arg | Phe | Pro | Thr | Gln |
|---|---|---|---|---|---|---|---|---|---|---|---|---|---|---|---|
|   |   | 115 |   |   |   |   | 120 |   |   |   |   | 125 |   |   |   |

| Val | Glu | Asp | Ser | Phe | Ala | Ala | Leu | Thr | Trp | Val | Ser | Glu | His | Ala | Ser |
|---|---|---|---|---|---|---|---|---|---|---|---|---|---|---|---|
| 130 |   |   |   |   | 135 |   |   |   |   | 140 |   |   |   |   |   |

| Glu | Leu | Gly | Val | Asp | Pro | Ala | Arg | Val | Ala | Val | Ala | Gly | Asp | Ser | Ala |
|---|---|---|---|---|---|---|---|---|---|---|---|---|---|---|---|
| 145 |   |   |   |   | 150 |   |   |   |   | 155 |   |   |   |   | 160 |

| Gly | Gly | Asn | Leu | Ala | Thr | Val | Met | Cys | Leu | Leu | Ala | Lys | Ala | Arg | Gly |
|---|---|---|---|---|---|---|---|---|---|---|---|---|---|---|---|
|   |   |   |   | 165 |   |   |   |   | 170 |   |   |   |   | 175 |   |

| Gly | Pro | Arg | Ile | Ala | Cys | Gln | Ala | Leu | Leu | Tyr | Pro | Val | Ala | Asp | Phe |
|---|---|---|---|---|---|---|---|---|---|---|---|---|---|---|---|
|   |   |   | 180 |   |   |   |   | 185 |   |   |   |   | 190 |   |   |

| Arg | Pro | Glu | Gln | Val | Tyr | Ala | Ser | His | Ala | Gln | Phe | Gly | Asp | Gly | Ser |
|---|---|---|---|---|---|---|---|---|---|---|---|---|---|---|---|
|   |   | 195 |   |   |   |   | 200 |   |   |   |   | 205 |   |   |   |

| Tyr | Phe | Leu | Ser | Ser | Lys | Asp | Met | Asp | Trp | Phe | Arg | Ala | Ser | Tyr | Phe |
|---|---|---|---|---|---|---|---|---|---|---|---|---|---|---|---|
|   | 210 |   |   |   |   | 215 |   |   |   |   | 220 |   |   |   |   |

| Thr | Asp | Val | Ala | Ser | Gln | Ala | Ala | Glu | Pro | Thr | Ala | Ser | Pro | Met | Ala |
|---|---|---|---|---|---|---|---|---|---|---|---|---|---|---|---|
| 225 |   |   |   |   | 230 |   |   |   |   | 235 |   |   |   |   | 240 |

| Thr | Thr | Asp | Leu | Ser | Gly | Leu | Pro | Pro | Ala | Leu | Val | Thr | Thr | Ala | Gly |
|---|---|---|---|---|---|---|---|---|---|---|---|---|---|---|---|
|   |   |   |   | 245 |   |   |   |   | 250 |   |   |   |   | 255 |   |

| Cys | Asp | Pro | Leu | Leu | Asp | Glu | Gly | Arg | Ala | Tyr | Ala | Asp | Arg | Leu | Lys |
|---|---|---|---|---|---|---|---|---|---|---|---|---|---|---|---|
|   |   |   | 260 |   |   |   |   | 265 |   |   |   |   | 270 |   |   |

| Ala | Ala | Gly | Val | Pro | Val | Asp | Tyr | Arg | Cys | Phe | Glu | Thr | Thr | Ile | His |
|---|---|---|---|---|---|---|---|---|---|---|---|---|---|---|---|
|   |   | 275 |   |   |   |   | 280 |   |   |   |   | 285 |   |   |   |

| Ala | Cys | Ala | Ser | Phe | Ala | Gly | Thr | Ile | Pro | Ala | Gly | Leu | Asp | Met | Leu |
|---|---|---|---|---|---|---|---|---|---|---|---|---|---|---|---|
|   | 290 |   |   |   |   | 295 |   |   |   |   | 300 |   |   |   |   |

| Gly | Phe | Val | Ala | Asp | Trp | Leu | Ala | Ala | His | Thr | Lys |
|---|---|---|---|---|---|---|---|---|---|---|---|
| 305 |   |   |   |   | 310 |   |   |   |   | 315 |   |

<210> SEQ ID NO 11
<211> LENGTH: 927
<212> TYPE: DNA
<213> ORGANISM: unknown
<220> FEATURE:
<221> NAME/KEY: source
<223> OTHER INFORMATION: /note="Description of unknown sequence:
      metagenomic expression library"

<400> SEQUENCE: 11
atgccattac atccccaagt caaagccgtt ctcgaactca tggaaaaagc cggaccgccg    60

```
atgcaccatc tttcaccgca acacgcgcgt gaacagattc tcgccatgcg tgccaccaag    120
ggcgaacctg agcccgtagg caaggtagaa gatcggacta tcaaagattc agcaggagat    180
attccggttc ggatttacac cccgaatggt cgtggcccat ttcctttact ggtgtatttt    240
cacggcggag ggtgggttgt cggcagtgtc gaaacggttg acgcttcatg tcgtgcgctc    300
acgaacctcg caaactgcgt tacggtctca gttgagtatc gactcgcgcc tgaacacaaa    360
ttcccggcac cggtggacga ttgctatgct gcaacccgat ggacagcctt gaatgctgct    420
tccttccacg ggacccggc acggattgct gtgggtggtg aaagtgcagg ggcaaacctt    480
gccgctgcgg tggcattgat ggcgcaagag cgcggggctc catctctcgt tcatcagttg    540
ttgttatatc cggtgacgaa ttacgcttct gatctgccgt ctcacaaagc gaatgccaca    600
gggtatttct tgacgacgga gatgatgcgg tggttttgga accattacct gcggaacgag    660
accgatggag aaaatcccct cgcttcacca ctgcgtgcca agcggttgca agggcttgct    720
ccagcgacga tctacaccgc agagtttgac ccgctacgag atgaaggtgc ggcatacgcg    780
accaaactcc gtgaagcggg aatcgctgtc gagtacacgt gctacgaggg tttgattcac    840
ggtttcatgg gaatggcgaa agctgtcgaa ccggcgaaga aggcactgga agatgccggt    900
gctgcgttgc ggaaggcgtt ggcgtag                                        927
```

<210> SEQ ID NO 12
<211> LENGTH: 308
<212> TYPE: PRT
<213> ORGANISM: unknown
<220> FEATURE:
<221> NAME/KEY: source
<223> OTHER INFORMATION: /note="Description of unknown sequence: metagenomic expression library"

<400> SEQUENCE: 12

```
Met Pro Leu His Pro Gln Val Lys Ala Val Leu Glu Leu Met Glu Lys
1               5                   10                  15

Ala Gly Pro Pro Met His His Leu Ser Pro Gln His Ala Arg Glu Gln
            20                  25                  30

Ile Leu Ala Met Arg Ala Thr Lys Gly Glu Pro Glu Pro Val Gly Lys
        35                  40                  45

Val Glu Asp Arg Thr Ile Lys Asp Ser Ala Gly Asp Ile Pro Val Arg
    50                  55                  60

Ile Tyr Thr Pro Asn Gly Arg Gly Pro Phe Pro Leu Leu Val Tyr Phe
65                  70                  75                  80

His Gly Gly Gly Trp Val Val Gly Ser Val Glu Thr Val Asp Ala Ser
                85                  90                  95

Cys Arg Ala Leu Thr Asn Leu Ala Asn Cys Val Thr Val Ser Val Glu
            100                 105                 110

Tyr Arg Leu Ala Pro Glu His Lys Phe Pro Ala Pro Val Asp Asp Cys
        115                 120                 125

Tyr Ala Ala Thr Arg Trp Thr Ala Leu Asn Ala Ala Ser Phe His Gly
    130                 135                 140

Asp Pro Ala Arg Ile Ala Val Gly Gly Glu Ser Ala Gly Ala Asn Leu
145                 150                 155                 160

Ala Ala Ala Val Ala Leu Met Ala Gln Glu Arg Gly Ala Pro Ser Leu
                165                 170                 175

Val His Gln Leu Leu Leu Tyr Pro Val Thr Asn Tyr Ala Ser Asp Leu
            180                 185                 190
```

-continued

```
Pro Ser His Lys Ala Asn Ala Thr Gly Tyr Phe Leu Thr Glu Met
        195                 200                 205

Met Arg Trp Phe Trp Asn His Tyr Leu Arg Asn Glu Thr Asp Gly Glu
    210                 215                 220

Asn Pro Leu Ala Ser Pro Leu Arg Ala Lys Arg Leu Gln Gly Leu Ala
225                 230                 235                 240

Pro Ala Thr Ile Tyr Thr Ala Glu Phe Asp Pro Leu Arg Asp Glu Gly
                245                 250                 255

Ala Ala Tyr Ala Thr Lys Leu Arg Glu Ala Gly Ile Ala Val Glu Tyr
                260                 265                 270

Thr Cys Tyr Glu Gly Leu Ile His Gly Phe Met Gly Met Ala Lys Ala
                275                 280                 285

Val Glu Pro Ala Lys Lys Ala Leu Glu Asp Ala Gly Ala Ala Leu Arg
    290                 295                 300

Lys Ala Leu Ala
305

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: misc_feature
<222> LOCATION: (1)..(1)
<223> OTHER INFORMATION: Xaa is a small amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 13

Xaa Xaa Ser Xaa Gly
1               5

<210> SEQ ID NO 14
<211> LENGTH: 4
<212> TYPE: PRT
<213> ORGANISM: Unknown
<220> FEATURE:
<221> NAME/KEY: source
<223> OTHER INFORMATION: /note=Description of unknown sequence:
      metagenomic expression library
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Gly Gly Gly Xaa
1

<210> SEQ ID NO 15
<211> LENGTH: 4
<212> TYPE: PRT
<213> ORGANISM: Unknown
<220> FEATURE:
<221> NAME/KEY: source
<223> OTHER INFORMATION: /note=Description of unknown sequence:
      metagenomic expression library
<220> FEATURE:
```

-continued

```
<221> NAME/KEY: misc_feature
<222> LOCATION: (2)..(3)
<223> OTHER INFORMATION: Xaa can be any naturally occurring amino acid

<400> SEQUENCE: 15

Ser Xaa Xaa Lys
1
```

POLYNUCLEOTIDES ENCODING ENANTIOSELECTIVE CARBOXYLESTERASES AND METHODS OF MAKING SAME

This application is the National Phase of International Application PCT/EP2007/003919 filed May 3, 2007 which designated the U.S. and that International Application was was not published under PCT Article 21(2) in English, and claims priority to European Patent Application Serial No. 06 00 9545.2, filed May 9, 2006.

The present invention relates to a polynucleotide encoding an enzyme having carboxylesterase [E.C. 3.1.1.1] activity, wherein the coding sequence is selected from the group consisting of (a) a polynucleotide encoding an amino acid sequence as depicted in any one of SEQ ID NOs: 2, 4, 6, 8, 10 and 12; (b) a polynucleotide having or comprising a nucleotide sequence encoding an enzyme, wherein the nucleic acid sequence is as shown in any one of SEQ ID NOs: 1, 3, 5, 7, 9 and 11; (c) a polynucleotide having or comprising a nucleotide sequence encoding a fragment or derivative of an enzyme encoded by a polynucleotide of (a) or (b), wherein in said derivative one or more amino acid residues are conservatively substituted compared to the amino acid sequence of (a); (d) a polynucleotide encoding an enzyme having carboxylesterase activity which polynucleotide is at least 66% identical to a polynucleotide encoding an enzyme as shown in one of SEQ ID NOs: 2, 4, 6, 8, 10 and 12; (e) a polynucleotide having or comprising a nucleotide sequence the complementary strand of which hybridizes to a polynucleotide as defined in any one of (a) to (d); and (f) a polynucleotide having or comprising a nucleotide sequence being degenerate to the nucleotide sequence of the polynucleotide of (d) or (e); or the complementary strand of such a polynucleotide of (a) to (f) or fragments thereof useful as specific probes or primers. The present invention also relates to a host genetically engineered with the polynucleotide of the present invention or the vector of the present invention. The present invention also relates to a process for producing a polypeptide having carboxylesterase [E.C. 3.1.1.1] activity, comprising culturing the host of the present invention and recovering the polypeptide produced by said host. Moreover, The present invention also relates to a process for producing bacteria or eukaryotic cells capable of expressing a polypeptide having carboxylesterase [E.C. 3.1.1.1] activity, the process comprising genetically engineering bacteria or eukaryotic cells with the vector of the present invention. Finally, the present invention relates to (poly)peptides, antibodies, compositions and various methods for the production of optically active compounds.

Several documents are cited throughout the text of this specification. The disclosure content of the documents cited herein (including any manufacturer's specifications, instructions, etc.) is herewith incorporated by reference.

The use of enzymes as biocatalyst in the chemical industry has markedly increased during the last 20 years [1]. Breakthroughs in the key biotechnological areas of a) genetic resource access b) enzyme screening and discovery and c) in vitro evolution of proteins to find and optimize enzymes to become near-ideally suited biocatalysts have been instrumental in pushing industrial biocatalysis to where it stands today [2]. However, the feasibility of new biocatalytic processes will often be determined by the availability of the appropriate biocatalyst [3].

Application of modern screening technology to biodiversity—nature's plethora of individual solutions to billion years of stringent selection for superior performance in ecological niches structured by a multitude of biophysical and biochemical pressures, is clearly a rewarding approach to find industrially relevant enzymes. Screening cultivable microorganisms is a powerful and still the most common way for obtaining biocatalysts. However cultivation is limited as most microorganisms cannot be cultivated using current technologies [2].

The development of techniques to directly extract, clone and recombinantly express genomic DNA from entire uncultured microbial consortia, the so called "metagenome" approach, allows the access to the "unseen" majority of microbial diversity and its enzymatic constituents. Basically microbial cells are lysed either still in the context of natural substrate or after physical separation to yield high molecular weight DNA. This DNA has to be purified from co-extracted inhibitors prior to proceeding with standard cloning procedures. Finally the metagenomic DNA end up being propagated and possibly expressed in cultivable surrogate hosts like E. coli to be subjected to screening or selection procedures [2].

Carboxylesterases [EC 3.1.1.1] and lipases [EC 3.1.1.3] represent a diverse group of hydrolytic enzymes catalysing the cleavage and formation of ester bonds. The discrimination of esterases and lipases is usually based on the acyl chain length of their ester substrates: while esterases hydrolyse preferentially esters of short chain water-soluble esters, lipases are capable of hydrolysing also water insoluble, emulsified long chain ester substrates.

Many esterases and lipases share the same characteristic α/β hydrolase fold [4], a three-dimensional structure composed of a central, mostly parallel β-sheet shielded against the solvent by α-helices. However, the primary structures of these proteins are very often rather different showing identity levels sometimes <30%. The catalytic triad is composed of Ser-Asp-His (Glu instead of Asp for some enzymes) and usually also a consensus sequence Sm-Xaa-Ser-Xaa-Gly (SEQ ID NO:13) is found around the active site serine where "Sm" is a small amino acid (usually a glycine) and "x" or "Xaa" is any amino acid. Beside the catalytic triad the so called oxyanion hole is essential for the enzymatic activity. Its function is to stabilize the oxyanions of the carboxylic acid oxygen of the tetrahedral intermediates formed during the catalytic process.

More recently, esterases have been identified containing a "GDSL"-motif around the active site serine as well as enzymes showing high homology to class C β-lactamases [5].

Based on the analysis of their amino acid sequence, Arpigny and Jaeger [6] suggested a classification for bacterial esterases and lipases which identified 8 families and 6 subfamilies. Family IV is characterised beside the conserved catalytic triad and the consensus sequence around the active site serine by a highly conserved "GGGXaa (SEQ ID NO:14)"-motif comprising part of the oxyanion hole [6]). This structural motif (GGGX) distinguishes family IV from all other esterases showing an α/β hydrolase fold and led to the classification of esterases in "GGGX"-type and "GX"-type esterases [7]. It was found that the presence of the GGGX-type motif correlates with the capability of these enzymes to hydrolyse the esters of tertiary alcohols (TAE) [8]. Tertiary alcohols (TA) and TAEs represent a very important group of molecules and constitute very useful synthons for the production of fine chemicals [9]. They are found in several natural products, e.g. α-terpineol and linalool, which is an important terpene alcohol of the flavour and fragrance industry. The two different stereoisomers of linalool, licareol (the (R)-(−) enantiomer) and coriandrol (the (S)-(+) enantiomer), differ in their fragrance so that it is desirable to separate the optical pure isomers for the production of flavour and fragrance compositions.

Family VIII comprises enzymes which show higher homology to class C β-lactamases than to other esterases. This family is characterised by the active site motif "Ser-Xaa-Xaa-Lys (SEQ ID NO:15)" which is typical for class C β-lactamases. Enzymes belonging to this esterase-family usually do not hydrolyse β-lactams. Furthermore, although these proteins are also α/β structures their β-sheets consist mainly of antiparallel β-strands and the catalytic serine—which is not part of a triad—is at the beginning of an α-helix adjacent to the central β-sheet [10]. Noteworthy, one member of this family, the esterase B from *Burkholderia gladioli*, has been demonstrated to be also capably of hydrolyzing TAEs [11].

In spite of their distribution throughout humans, animals, plants and microorganisms [5], their physiological function remains to be elucidated [12]. Nevertheless, due to their high stability, the fact that they do not require cofactors, their activity in organic solvents, and their high regio- and enantioselectivity, carboxylesterases appear to be attractive biocatalysts for the production of optically pure compounds in fine chemicals synthesis [5].

Products intended for use in biological systems must often by synthesized in a particular enantiomeric form due to preferences that correlate with the "handedness" (i.e., optical rotation) of the molecule. For example, only the (S)-form of the widely prescribed anti-inflammatory Naproxen (2-(6-methoxy-2-naphthyl)-propionic avid) is clinically effective. The (R)-form is toxic [13]. Therefore, the drug must be supplied such that the (S)-enantiomer, and not the (R)-enantiomer, is highly enriched in the final product. A similar situation exists for many other pharmaceutical and agricultural chemicals. However, the synthesis chemist is often faced with a difficult problem because most chemical catalysts do not discriminate by optical form. In fact, it is very difficult to synthesize a single enantiomer. Moreover, because enantiomers, by definition, have identical physical properties and differ only in the direction that they rotate plane polarized light, separation of individual enantiomers from a mixture of (S)- and (R)-enantiomers is difficult.

Thus, the technical problem underlying the present invention was to provide means and methods for the improvement of the spectrum of enzymes capable of the conversion of a multiplicity of substrates with high reaction rates or capable of the enantioselective conversion of racemic starting material into products of interest. The provision of such enzymes may increase the efficiency of the conversion and further reduce the cost for the industrial application of the produced synthons.

The solution to this technical problem is achieved by providing the embodiments characterized in the claims.

According, the present invention relates to a polynucleotide encoding an enzyme having carboxylesterase [E.C. 3.1.1.1] activity, wherein the coding sequence is selected from the group consisting of (a) a polynucleotide encoding an amino acid sequence as depicted in any one of SEQ ID NOs: 2, 4, 6, 8, 10 and 12; (b) a polynucleotide having or comprising a nucleotide sequence encoding an enzyme, wherein the nucleic acid sequence is as shown in any one of SEQ ID NOs: 1, 3, 5, 7, 9 and 11; (c) a polynucleotide having or comprising a nucleotide sequence encoding a fragment or derivative of an enzyme encoded by a polynucleotide of (a) or (b), wherein in said derivative one or more amino acid residues are conservatively substituted compared to the amino acid sequence of (a); (d) a polynucleotide encoding an enzyme having carboxylesterase activity which polynucleotide is at least 66% identical to a polynucleotide encoding an enzyme as shown in one of SEQ ID NOs: 2, 4, 6, 8, 10 and 12; (e) a polynucleotide having or comprising a nucleotide sequence the complementary strand of which hybridizes to a polynucleotide as defined in any one of (a) to (d); and (f) a polynucleotide having or comprising a nucleotide sequence being degenerate to the nucleotide sequence of the polynucleotide of (d) or (e); or the complementary strand of such a polynucleotide of (a) to (f) or fragments thereof useful as specific probes or primers.

The polynucleotides provided by the present invention are listed herein as SEQ ID NO: 1, SEQ ID NO:3, SEQ ID NO: 5, SEQ ID NO: 7, SEQ ID NO: 9. SEQ ID NO: 11 and the (poly)peptides provided by the present invention are listed herein as SEQ ID NO: 2, SEQ ID NO: 4, SEQ ID NO: 6, SEQ ID NO: 8, SEQ ID NO: 10 and SEQ ID NO: 12. Polynucleotide sequences and polypeptide sequences are depicted in FIGS. 1 to 12.

The enzymes according to SEQ ID NO: 4, 8, 10 and 12 were denoted to belong to the family IV of bacterial lipolytic enzymes, those according to SEQ ID NO: 2 and 6 were denoted to be members of family VIII.

In accordance with the present invention the term "polynucleotide" defines a nucleic acid molecule consisting of more than 30 nucleotides. The group of molecules designated as "polynucleotides" also comprises complete genes. Also included by said definition are vectors such as cloning and expression vectors.

As used herein, the term "oligonucleotides" describes nucleic acid molecules consisting of at least ten and up to 30 nucleotides.

Nucleic acid molecules, in accordance with the present invention, include DNA, such as cDNA or genomic DNA, RNA (e.g. mRNA), also in synthetic or semisynthetic form, further synthetic or semisynthetic derivatives of DNA or RNA (e.g. PNA or phosphorothioates) and mixed polymers, both sense and antisense strands. They may contain additional non-natural or derivatized nucleotide bases, as will be readily appreciated by those skilled in the art. In a preferred embodiment the polynucleotide or the nucleic acid molecule(s) is/are DNA.

For the purposes of the present invention, a peptide nucleic acid (PNA) is a polyamide type of DNA analog and the monomeric units for the derivatives of adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex.

Also, the absence of charge groups in PNA means that hybridization can be done at low ionic strengths and reduce possible interference by salt during the analysis.

In those embodiments where the polynucleotide comprises (rather than have) the recited sequence, additional nucleotides extend over the specific sequence either on the 5' end or the 3' end or both. Those additional polynucleotides may be of heterologous or homologous nature and may comprise stretches of about 50 to 500 nucleotides although higher or lower values are not excluded. In the case of homologous sequences, those embodiments do not include complete genomes and are generally confined to about 1500 additional nucleotides at the 5' and/or the 3' end. Additional heterologous sequences may include heterologous promoters which are operatively linked to the coding sequences of the invention.

The term "polypeptide" as used herein describes a group of molecules which consist of more than 30 amino acids. In accordance with the invention, the group of polypeptides comprises "proteins" as long as the proteins consist of a single polypeptide. Also in line with the definition the term "polypeptide" describes fragments of proteins as long as these fragments consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. Homodimers, trimers etc. of fusion proteins giving rise or corresponding to enzymes such as the carboxylesterases of the present invention also fall under the definition of the term "protein". Furthermore, peptidomimetics of such proteins/polypeptides wherein amino acid(s) and/or peptide bond(s) have been replaced by functional analogs are also encompassed by the invention. Such functional analogues include all known amino acids other than the 20 gene-encoded amino acids, such as selenocysteine. The terms "polypeptide" and "protein" also refer to naturally modified polypeptides/proteins wherein the modification is effected e.g. by glycosylation, acetylation, phosphorylation and the like. Such modifications are well known in the art.

The term "enzyme" defines in the context of the invention a polypeptide, polypeptides and/or protein(s), comprising either the triad of active site residues with the active site serine embedded in the consensus sequence "Sm-Xaa-Ser-Xaa-Gly (SEQ ID NO:13)" typical of families I, III, IV V, VI and VII of bacterial lypolytic enzymes [6] with "Sm" being a small amino acid and "x" being any amino acid or the N-terminally located active site motif "Ser-Xaa-Xaa-Lys (SEQ ID NO:15)" of family VIII of bacterial lypolytic enzymes [6]. Preferably, the said polypeptide, protein or fragment thereof has catalytic activity. An enzyme in accordance with the present invention is preferably capable of hydrolysing tributyrin.

The term "carboxylesterase" refers to an enzyme with the systematic name "carboxylic-ester hydrolase", i.e. an enzyme having an activity which may e.g. be described as:

Reaction: A carboxylic ester+H₂O=an alcohol+a carboxylate

The IUBMB Enzyme Nomenclature refers to carboxylesterases as "EC 3.1.1.1". Examples of such carboxylesterases are: ali-esterase; B-esterase; monobutyrase; cocaine esterase; procaine esterase; methylbutyrase; vitamin A esterase; butyryl esterase; carboxyesterase; carboxylate esterase; carboxylic esterase; methylbutyrate esterase; triacetin esterase; carboxyl ester hydrolase; butyrate esterase; methylbutyrase; α-carboxylesterase; propionyl esterase; non-specific carboxylesterase; esterase D; esterase B; esterase A; serine esterase; carboxylic acid esterase; cocaine esterase.

Methods and algorithms for exchanging one or more nucleotides in the polynucleotide in item (c), supra, wherein the exchange gives rise to a conservative substitution of one or more amino acid residues in a given polypeptide are known in the art; see e.g. Barettino et al. 1994 [14], Urban et al. 1997 [15] or Seyfang & Jin 2004 [16].

In accordance with the present invention, the term "percent identity" describes the number of matches ("hits") of identical nucleotides/amino acids of two or more aligned nucleic acid or amino acid sequences as compared to the number of nucleotides making up the overall length of the nucleic acid or amino acid sequences (or the overall compared part thereof). In other terms, using an alignment, for two or more sequences or subsequences the percentage of amino acid residues or nucleotides that are the same (e.g., 60% or 65% identity) may be determined, when the (sub)sequences are compared and aligned for maximum correspondence over a window of comparison, or over a designated region as measured using a sequence comparison algorithm as known in the art, or when manually alignment and visually inspected. This definition also applies to the complement of a test sequence. Preferred polynucleotides/polypeptides in accordance with the invention are those where the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on the CLUSTALW computer program (Thompson Nucl. Acids Res. 2 (1994), 4673-4680) or FASTA [17], as known in the art.

The present invention refers to polynucleotides encoding an enzyme having carboxylesterase activity. Particularly preferred are polynucleotides which are at least 66% identical to a polynucleotide encoding an enzyme as shown in one of SEQ ID NOs: 2, 4, 6, 10 and 12. More preferred are, with increasing preference, polynucleotides which are at least 70%, at least 80%, at least 85%, at least 90%, at least 95%, at least 97, at least 99% sequence identity. Tables 1.1a to 1.1f show a comparison of the polynucleotides of the present invention with the next sequence neighbours. The analysis was performed using the Fasta algorithm [17] using GenBank database [18], Release 152.0, (released on Feb. 18, 2005).

TABLE 1.1a

Sequence identity of the polynucleotide according to SEQ ID NO: 1 (Est1)

| next neighbour | gene identifier | organism | Identity [%] | overlap | reference |
|---|---|---|---|---|---|
| cyclododecanone oxidation gene cluster | AY052630 | *Rhodococcus ruber* strain SC1 | 65.483 | 1098 nt 16-1102: 2527-3621 | Kostichka et al.[19] |
| beta-lactamase | XM_748568 | *Aspergillus fumigatus* Af293 | 60.718 | 1087 nt 14-1084: 26-1095 | Nierman et al.[20] |

TABLE 1.1b

Sequence identity of the polynucleotide according to SEQ ID NO: 3 (Est5)

| Next neighbour | gene identifier | organism | Identity [%] | overlap | reference |
|---|---|---|---|---|---|
| esterase | DQ025532 | Uncultured bacterium | 59.729 | 812 nt 93-1087: 460-1262 | Kim et al.[21] |
| brefeldin A esterase | AF056081 | *Bacillus subtilis* | 59.424 | 382 nt 712-1083: 757-1134 | Wei et al.[22] |

TABLE 1.1c

Sequence identity of the polynucleotide according to SEQ ID NO: 5 (Est7)

| Next neighbour | gene identifier | organism | Identity [%] | overlap | reference |
|---|---|---|---|---|---|
| chromosome II, complete sequence | CP000125 | *Burkholderia pseudomallei* 1710b | 63.768 | 828 nt (865-56: 476237-477045) | Rashamuse, K. J. and Cowan, D. A.[23] |
| EstBL | AY965997 | *Burkholderia cepacia* | 64.619 | 814 nt (70-866: 184-978) | Woods, D. E. and Nierman, W. C[24] |

TABLE 1.1d

Sequence identity of the polynucleotide according to SEQ ID NO: 7 (Est8)

| next neighbour | Gene identifier | organism | Identity [%] | overlap | Reference |
|---|---|---|---|---|---|
| putative oxidoreductase and lipase/esterase genes | AY496578 | Uncultured bacterium clone pELP141 | 64.684 | 90 nt (85-869: 1172-1959) | Lee et al.[25] |
| oxidoreductase gene and lipase/esterase gene | AY496577 | Uncultured bacterium clone pELP11B | 64.899 | 792 nt (85-869: 685-1472) | Lee et al.[25] |

TABLE 1.1e

Sequence identity of the polynucleotide according to SEQ ID NO: 9 (Est56)

| next neighbour | gene identifier | organism | Identity [%] | overlap | Reference |
|---|---|---|---|---|---|
| chromosome I, complete sequence | CP000086 | *Burkholderia thailandensis* | 57.274 | 983 nt (2-946: 2427922-2428870) | Kim et al.[26] |
| chromosome 1, complete sequence | CP000010 | *Burkholderia mallei* ATCC 23344 | 57.508 | 979 nt (938-1: 1484064-1485007) | Nierman et al.[27] |

TABLE 1.1f

Sequence identity of the polynucleotide according to SEQ ID NO: 11 (Est63)

| next neighbour | gene identifier | organism | Identity [%] | overlap | Reference |
|---|---|---|---|---|---|
| complete genome | AP006840 | *Symbiobacterium thermophil* AM 14863 | 58.972 | 914 nt (922-17: 2270308-2271216) | Ueda et al.[28] |
| chromosome 2, complete sequence | CP000091 | *Ralstonia eutropha* JMP134 | 58.915 | 903 nt (28-920: 2253319-2254208) | Copeland et al.[29] |

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. All those programs may be used for the purposes of the present invention. All of the above programs can be used in accordance with the invention.

The term "hybridizes/hybridizing" as used herein refers to a pairing of a polynucleotide to a (partially) complementary strand of this polynucleotide which thereby form a hybrid. Said complementary strand polynucleotides are, e.g. the polynucleotides described in item (e), supra, or parts of polynucleotides comprising at least 10, preferably at least 15 such as at least 25 consecutive nucleotides thereof, if used as primers or probes. Said complementary polynucleotides may be useful as probes in Northern or Southern blot analysis of RNA or DNA preparations, PCRs and the like or primer extension protocols respectively. In this connection, the term "fragments thereof useful as specific probes or primers" refers to nucleic acid molecules the sequence of which is uniquely fitting to (hybridizing to/complementary to preferably 100%) the sequences of the nucleic acid molecules described in accordance with the present invention, but not to prior art sequences. The skilled person can identify such fragments by simple sequence alignments. For example, if there is a 100% stretch of identity with a prior art sequence, the addition of a further nucleotide to that sequence of identity will yield a novel sequence which is encompassed by the present invention, since it is to 100% complementary to the polynucleotide of the invention but not to the prior art sequence. Hybridizing polynucleotides of the present invention to be used as a probe in Southern or Northern blot preferably comprises at least 100, more preferably at least 200, and most preferably at least 500 nucleotides in length. As regards those polynucleotides or pairs of polynucleotides that hybridize to the complementary strand of the specifically disclosed polynucleotide sequences and retain or essentially retain carboxylesterase activity must encode at least the amino acids of the catalytic triad and the oxyanion hole of the enzyme.

Preferably, the term "polynucleotide fragment" or "fragment" refers to a fragment of the polynucleotide of the present invention lacking at least 1 nucleotide. The term "at least 1 nucleotide" means e.g. up to 1, up to 10, up to 20, up to 50 or up to 100 nucleotides. Said fragment may correspond to a 5' and/or 3' deletion of the full-length polynucleotide of the present invention. In addition or alternatively, the deletion may be located in an internal position. The deletion may affect a contiguous number of residues, however, it is also envisaged that the fragment is the polynucleotide of the present invention having deletions of various, also non-contiguous residues. Preferably, said fragment encodes a protein or polypeptide with carboxylesterase activity. The activity may not necessarily be of the same degree as the full-length or wild-type carboxylesterase as long as some activity is retained.

It is well known in the art how to perform hybridization experiments with nucleic acid molecules. Correspondingly, the person skilled in the art knows what hybridization conditions s/he has to use to allow for a successful hybridization in accordance with item (e), above. The establishment of suitable hybridization conditions is referred to in standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). In one preferred embodiment, the hybridization is effected is under stringent conditions.

"Stringent hybridization conditions" refers to conditions which comprise, e.g. an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulphate, and 20 µg/ml denatured, sheared salmon sperm DNA, followed by washing the filters in 0.1×SSC at about 65° C. Said conditions for hybridization are also known by a person skilled in the art as "highly stringent conditions for hybridization". Also contemplated are nucleic acid molecules that hybridize to the polynucleotides of the invention at lower stringency hybridization conditions ("low stringency conditions for hybridization"). Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 0.2M NaH$_2$PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve an even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The embodiment recited herein above preferably refers to highly stringent conditions and alternatively to conditions of lower stringency.

The term "coding sequence" as used herein refers to the coding sequence of the carboxylesterase of the present invention or a fragment or derivative thereof. Said term relates to the genomic coding sequence as well as the coding sequence in a RNA or cDNA molecule.

When testing the carboxylesterases of the present invention, the inventors surprisingly discovered that their enzymatic activities met the requirements outlined above.

A number of tests have been performed in order to document the kinetic properties of the enzymes of the present invention. The enzymes according to SEQ ID NO: 10 (Est 56) and to SEQ ID NO: 12 (Est 63) hydrolysed the substrate 1-phenyl-1-ethylacetate enantioselectively with an E-value of 20 and 12, respectively, with a preference for the (R)-enantiomer. The enzymes according to SEQ ID NO: 6 (Est 7) yielded an E-values of 68 with a preference for the (S)-enantiomer. The recombinant pig liver esterase (rPLE) was tested in form of different enzyme preparations for the stereospecific hydrolysis of this substrate [30]. The highest enantioselectivity was observed with Chirazyme E1 (Roche Diagnostics) with an E-value of 7.9. The selectivity of the rPLE was improved by site directed mutagenesis [31] with the best variant (PLE-PICEa) exhibiting an enantioselectivity with an E-value of 54 for the (R)-configuration of the product alcohol.

The optical purity of chiral compounds is usually expressed as percent enantiomeric excess (% ee). % ee values can be calculated from the molar ratio of each enantiomer, Eq. 1. In practice, the peak areas for each enantiomer are obtained by gas chromatography or HPLC analysis using a chiral column and are then used to calculate % ee instead of the molar ratios.

Per definition, a racemate has a % ee value of 0, optically pure compounds have a % ee value of 100.

$$\% \ ee = \frac{X_A - X_B}{X_A + X_B} * 100 \qquad Eq..1$$

$X_A$=Concentration of enantiomer A; $X_B$=Concentration of enantiomer B

Enzymatic syntheses of optically active compounds either start from racemic mixtures or from prostereogenic (prochiral) precursors. The latter ideally yields a product with 100% ee at 100% yield. In contrast, a kinetic resolution will only lead to a yield of 50%. Methods to increase the yield include racemization of the non-wanted enantiomer, by using a racemase or chemical racemization or by performing a so-called dynamic kinetic resolution (DKR). The requirements for a DKR are: (1), the substrate must racemize faster than the subsequent enzymatic reaction, (2), the product must not racemize, and (3), as in any asymmetric synthesis, the enzymatic reaction must be highly stereoselective.

The stereopreference (enantiopreference) of an enzyme is described by the enantiomeric excess (ee) of the enantiomers. However, this term is not sufficient to describe the enantioselectivity of an enzyme.

In a kinetic resolution, the enantiomeric purity of the product and starting material varies as the reaction proceeds. To more conveniently compare kinetic resolutions, Charles Sih's group developed equations to calculate their inherent enantioselectivity [32,33]. This enantioselectivity, called the enantiomeric ratio, E, measures the ability of the enzyme to distinguish between enantiomers. A non-selective reaction has an E of 1, while resolutions with E's above 20 (better E>5) are useful for synthesis. To calculate E, one measures two of the three variables: enantiomeric purity of the starting material ($ee_s$), enantiomeric purity of the product ($ee_p$), and extent of conversion (c) and uses one of the three equations below (Eq. 2). Often enantiomeric purities are more accurately measured than conversion; in these cases, the third equation is more accurate. Note that these equations are only applicable to irreversible reactions. In other cases, the equilibrium constant must be determined and alternative equations must be used.

$$E = \frac{\ln[1 - c(1 + ee_p)]}{\ln[1 - c(1 - ee_p)]}; \qquad Eq..2$$

$$E = \frac{\ln[(1 - c)(1 - ee_s)]}{\ln[(1 - c)(1 + ee_s)]};$$

$$E = \frac{\ln\left[\frac{1 - ee_s}{1 + (ee_s/ee_p)}\right]}{\ln\left[\frac{1 + ee_s}{1 + (ee_s/ee_p)}\right]}$$

High E values (≥100) are less accurately measured than low or moderate E values because the enantiomeric ratio is a logarithmic function of the enantiomeric purity. When E≥100, small changes in the measured enantiomeric purities give large changes in the For the enzyme according to SEQ ID NO: 6 (Est 7) an enantioselectivity in the kinetic resolution of (R,S)-1-phenyl-1-propylacetate with an E-value of 19 was found with a preference for the (S)-enantiomer. The enzymes according to SEQ ID NO: 10 (Est 56) and SEQ ID NO: 4 (Est 5) showed E-values of 43 and 7, respectively, with the same substrate but with a enantiopreference for the (R)-stereoisomer. The rPLE was tested in form of different enzyme preparations for the stereospecific hydrolysis of this substrate [34]. The highest enantioselectivity was observed with an enzyme preparation from Fluka with an E-value of 2.2. The selectivity of the rPLE was improved by site directed mutagenesis [31] with the best variant exhibiting an enantioselectivity with an E-value of 6 for the (R)-configuration of the product alcohol.

For the enzyme according to SEQ ID NO: 4 (Est 5) an enantioselectivity in the kinetic resolution of (R,S)-1-phenyl-2-pentylacetate with an E-value of 9 was found with a preference for the (R)-enantiomer. The enzyme according to SEQ ID NO: 12 (Est 63) showed an E-values of 6 with the same substrate but with a enantiopreference for the (S)-stereoisomer. The rPLE was tested in form of different enzyme preparations for the stereospecific hydrolysis of this substrate [34]. The rPLE displayed an enantioselectivity with an E-value of 16.7 and a preference for the (S)-configuration of the product alcohol.

The enzyme according to SEQ ID NO: 4 (Est 5) is characterised by the ability to hydrolyse (R,S)-1-phenyl-2-propylacetate enantioselectively with an E-value of 40 and a preference for the (R)-enantiomer. The enzymes according to SEQ ID NO: 2 (Est 1) and SEQ ID NO: 6 (Est 7) showed a selectivity of E=33 and 9, respectively, with a preference for the (S)-enantiomer. Musidlowska et al [30] reported that the rPLE hydrolyzed preferentially the (S)-enantiomer of this substrate with an E-value of 12.6. This selectivity could be improved to an E-value of 13 by a variant of rPLE which was derived from rPLE by site directed mutagenesis [31]. The lipase A (lipA) from *Bacillus subtilis* showed an E-value of 39.1 with a preference for the (S)-enantiomer [35].

The enzyme according to SEQ ID NO: 6 (Est 7) showed an enantiopreference for the (S)-isomer of (R,S)-1-phenyl-3-butylacetate with an E-value of 19. For the enzymes according to SEQ ID NO: 10 (Est 56) and Seq-ID No. 8 (Est 8) E-values of 15 and 8, respectively, were observed in the kinetic resolution of this substrate with a preference for the (R)-enantiomer. The rPLE showed an E-value of 6.3 with a preference for the (S)-enantiomer of the product alcohol [34].

2-Alkylidenetetrahydrofurans represent important versatile synthetic building blocks for the synthesis of pharmacologically relevant natural products and natural product analogues. For example, they can be used as direct precursors for the preparation of functionalized tetrahydrofurans and furans which occur in a variety of natural products such as nactin derivatives, tetronasin, tetronomycin or methyl nonactate [36-39]. In addition, they have been used for the synthesis of terpenes [40a,b] and medium-sized lactones [41].

2-Alkylidenetetrahydrofurans are interesting also in their own right; they are of considerable pharmacological relevance [42] and occur in a number of natural products. This includes for example charlic and charolic acids and terrestric acid which are metabolites of *Penicillium charlesii* and *Penicillium terrestre*, respectively [43]. Bicyclic 2-alkylidenetetrahydrofurans have been used as direct precursors for the synthesis of the natural spiroketal chalcogran [44]. Functionalized furans are of considerable pharmacological relevance and occur in a variety of natural products, such as terpenes. They include, for instance, the calicogorgins, furan fatty acids, cytotoxic furanocembranes, gersolanes, pseudopteranes, rosefuran, agassizin, furodysin, mikanifuran, and α-clausenan [45,46].

The use of enantioselective esterases for the kinetic resolution of 2-Alkylidenetetrahydrofurans allows the production of these important building blocks enantiomerically pure, in contrast to conventional chemical methods.

The kinetic resolution of (R,S)-tetrahydrofuran-2-yl-ethylacetate by the enzyme according SEQ ID NO: 10 (Est 56) yielded an E-value of 15.

The kinetic resolution of (R/S)-tetrahydrofuran-2-yl-methylacetate by the enzyme according SEQ ID NO: 10 (Est 56) yielded an E-value of 100, whereas the enzyme according to SEQ ID NO: 12 (Est63) showed an enantioselectivity with an E-value of 9.

Table 1.2 summarizes the properties of the enzymes according to Seq. ID-No. 2 to 12.

encoding the carboxylesterase of the present invention. In contrast, a polynucleotide is "homologous" when it is derived from the same cell or organism as the sequence encoding the carboxylesterase of the invention. "Homologous" with respect to the host but located in a different genomic environment than the naturally occurring counterpart of said nucleotide sequence means that, if the nucleotide sequence is homologous with respect to the host (i.e. is naturally present in the same strain or species), it is not located in its natural location in the genome of said host. In particular it may be surrounded by different genes. In this case the nucleotide sequence may be either under the control of its own promoter or under the control of a heterologous promoter. The location of the introduced nucleic acid molecule can be determined by the skilled person by using methods well-known in the art, including Southern blotting. The polynucleotide(s) according to the invention which is/are present in the host may either be integrated into the genome of the host or be maintained extra-chromosomally. With respect to the first option, it is also to be understood that the polynucleotide or pairs of polynucleotides of the invention can be used to restore or create a mutant gene via homologous recombination.

In a preferred embodiment the heterologous or homologous polynucleotide encodes a polypeptide. Examples of heterologous polypeptides are NusA from *E. coli*, glutathion S-transferase from *Schistosoma japonicum* or the maltose binding protein from *E. coli* all of which might increase the solubility of the carboxylesterase.

The present invention also relates to a vector containing the polynucleotide of the present invention. Preferably, the a vector is a plasmid, cosmid, virus, bacteriophage or another vector used e.g. conventionally in genetic engineering.

| enzyme | Seq ID No. | source | tributyrin-hydrolysis | lipase family$ | GGGX-type esterase& | β-lactamase type esterase$ | enantioselective conversion of [E-value and enantiopreference in brackets] |||||||
|---|---|---|---|---|---|---|---|---|---|---|---|---|---|
| | | | | | | | A | B | C | D | E | F | G |
| Est1 | 2 | Mg§ | + | VIII | | + | | | | 33 (S) | | | |
| Est5 | 4 | Mg§ | + | IV | + | | | 7 (R) | 9 (R) | 40 (R) | | | |
| Est7 | 6 | Mg§ | + | VIII | | + | 68 (S) | 19 (S) | | 9 (S) | 19 (S) | | |
| Est8 | 8 | Mg§ | + | IV | + | | | | | | 8 (R) | | |
| Est56 | 10 | Mg§ | + | IV | + | | 20 (R) | 43 (R) | | | 15 (R) | 15 (ε) | 100 (ε) |
| Est63 | 12 | Mg§ | + | IV | + | | 12 (R) | | 6 (S) | | | | 9 (ε) |

§metagenome
$according to reference [6]
&according to reference [7]
εabsolute configuration unknown
A: (R,S)-1-phenyl-1-ethylacetate
B: (R,S)-1-phenyl-1-propylacetate
C: (R,S)-1-phenyl-2-pentylacetate
D: (R,S)-1-phenyl-2-propylacetate
E: (R,S)-1-phenyl-3-butylacetate
F: (R,S)-tetrahydrofuran-2-yl-ethylacetate
G: (R,S)-tetrahydrofuran-2-yl-methylacetate In a preferred embodiment of the present invention, said coding region is fused with a heterologous or homologous polynucleotide. This heterologous or homologous polynucleotide may or may not be or comprise a coding region. The polynucleotide and/or the encoded enzyme having carboxylesterase activity is/are either heterologous with respect to the host or is/are homologous with respect to the host but located in a different genomic environment than the naturally occurring counterpart of said nucleotide sequence. A polynucleotide is "heterologous" when it is derived from a cell or organism belonging to a different strain (preferably to a different species) with regard to the origin of the sequence The polynucleotide of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega).

Examples for plasmid vectors suitable for *Pichia pastoris* comprise e.g. the plasmids pAO815, pPIC9K and pPIC3.5K (all Invitrogen).

The polynucleotide of the present invention referred to above may also be inserted into vectors such that a translational fusion with another polynucleotide is generated. The other polynucleotide may encode a protein which may e.g. increase the solubility and/or facilitate the purification of the fusion protein. Non-limiting examples include pET32, pET41, pET43.

For vector modification techniques, see Sambrook and Russel (2001), loc. cit. Generally, vectors can contain one or more origin of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the polynucleotide of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Possible examples for regulatory elements ensuring the initiation of transcription comprise the cytomegalovirus (CMV) promoter, SV40-promoter, RSV-promoter (Rous sarcome virus), the lacZ promoter, the gai10 promoter, human elongation factor 1α-promoter, CMV enhancer, CaM-kinase promoter, the Autographa californica multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the polynucleotide.

Furthermore, it is preferred that the vector of the invention comprises a selectable marker. Examples of selectable markers include neomycin, ampicillin, and hygromycin resistance and the like. Specifically-designed vectors allow the shuttling of DNA between different hosts, such as bacteria-fungal cells or bacteria-animal cells.

An expression vector according to this invention is capable of directing the replication, and the expression, of the polynucleotide and encoded enzyme of this invention. Suitable expression vectors which comprise the described regulatory elements are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11, pJOE, the pBBR1-MCS-series, pJB861, pBSMuL, pBC2, pUCPKS, pTACT1 or, preferably, the pET vector (Novagen).

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as eukaryotic expression system for the nucleic acid molecules of the invention.

The present invention also relates to a host, genetically engineered with the polynucleotide of the present invention or the vector of the present invention. Said host may be produced by introducing said polynucleotide or vector(s) into a host which upon its/their presence mediates the expression of the enzyme having carboxylesterase activity. The host may be any prokaryote or eukaryotic cell. A suitable eukaryotic host may be a mammalian cell, an amphibian cell, a fish cell, an insect cell, a fungal cell or a plant cell. A eukaryotic cell may be an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such as a human cell. The cell may be a part of a cell line.

The host may be any prokaryote or eukaryotic cell. A suitable eukaryotic host may be a mammalian cell, an amphibian cell, a fish cell, an insect cell, a fungal cell or a plant cell.

Suitable prokaryotes/bacteria are those generally used for cloning like *E. coli* (e.g., *E coli* strains HB101, DH5a, XL1 Blue, Y1090 and JM101), *Salmonella typhimurium, Serratia marcescens, Burkholderia glumae, Pseudomonas putida, Pseudomonas fluorescens, Pseudomonas stutzeri, Streptomyces lividans, Lactococcus lactis, Mycobacterium smegmatis* or *Bacillus subtilis*. Preferred examples for hosts to be genetically engineered with the polynucleotide of the invention are *E. coli* and *B. subtilis*.

In a preferred embodiment of the present invention, said host is a prokaryotic host selected from the group consisting of *E. coli, Bacillus* sp., *Pseudomonas* sp., *Streptomyces* sp., *Mycobacterium* sp., *Caulobacter* sp., *Rhodobacter* sp., *Lactococcus* sp., *Burkholderi* sp. and *Ralstonia* sp.

In another preferred embodiment of the present invention, said host expresses (a) the polypeptide encoded by the polynucleotide of the present invention or the vector of the present invention and (b) one or more additional enzyme(s) wherein said enzymes in toto catalyze a multi-step conversion of a substrate or contribute thereto.

In a more preferred embodiment of the present invention, the one or more additional enzyme(s) is/are a Baeyer-Villiger monooxygenase and, optionally, an enzyme for the regeneration of the cofactor NAD(P)H.

The present invention also relates to a process for producing a polypeptide having carboxylesterase [E.C. 3.1.1.1] activity, comprising culturing the host of the present invention and recovering the polypeptide produced by said host.

Said polypeptide may comprise additional N- or C-terminal amino acid sequences. Such polypeptides are sometimes also referred to as fusion proteins.

A large number of suitable methods exist in the art to produce polypeptides (or fusion proteins) in appropriate hosts. If the host is a unicellular organism such as a prokaryote, a mammalian or insect cell, the person skilled in the art can revert to a variety of culture conditions. Conveniently, the produced protein is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of protein in hosts as indicated above. For example, nucleic acid sequences comprising the polynucleotide according to the invention can be synthesized by PCR, inserted into an expression vector. Subsequently a suitable host may be transformed with the expression vector. Thereafter, the host is cultured to produce the desired polypeptide(s), which is/are isolated and purified.

An alternative method for producing the carboxylesterase of the invention is in vitro translation of mRNA. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega). These systems allow the expression of recombinant polypeptides upon the addition of cloning vectors, DNA fragments, or RNA sequences containing coding regions and appropriate promoter elements.

In addition to recombinant production, fragments of the protein, the fusion protein or fragments of the invention may e.g. be produced by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154).

Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used.

Protein isolation and purification can be achieved by any one of several known techniques; for example and without limitation, ion exchange chromatography, gel filtration chromatography and affinity chromatography, high pressure liquid chromatography (HPLC), reversed phase HPLC, and preparative disc gel electrophoresis. Protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein.

The present invention also relates to a process for producing bacteria or eukaryotic cells capable of expressing a polypeptide having carboxylesterase [E.C. 3.1.1.1] activity, the process comprising genetically engineering bacteria or eukaryotic cells with the vector of the present invention. The term "genetic engineering" refers to the process of bringing into a cell genetic information or modifying the genetic information of a cell. This is generally accomplished by transfecting or transforming a host cell with a nucleic acid molecule. Introduction of a construct into the host cell can be effected by calcium phosphate transfection, DEAE-dextran mediated transfection, cationic lipid-mediated transfection, electroporation, transduction, infection or other methods. Such methods are described in many standard laboratory manuals, such as Sambrook et al., "Molecular Cloning, A Laboratory Manual"; ISBN: 0879695765, CSH Press, Cold Spring Harbor, 2001. Said nucleic acid molecule introduced into the host cell comprises an open reading frame encoding the polypeptide of the present invention.

The present invention also relates to a polypeptide comprising the amino acid sequence encoded by a polynucleotide of the present invention or obtainable by the process of the present invention. In addition of residues derived from a carboxylesterase, the polypeptide of the present invention may contain additional, heterologous sequences. Often, but not necessarily, these additional sequences will be located at the N- or C-terminal end of the polypeptide, in other words the polypeptide may be a fusion protein. It may be convenient to initially express the polypeptide as a fusion protein from which the additional amino acid residues can be removed, e.g. by expression of a proteinase capable of specifically trimming the polypeptide of the present invention. The additional heterologous sequences may help in the expression or purification of the present invention. In addition, heterologous sequences may assist in attaching the polypeptide of the present invention to a carrier.

The present invention also relates to an antibody specifically binding to the polypeptide of the present invention. It is preferred that the antibody binds to the polypeptides or fusion protein of the invention in the form having carboxylesterase activity. In the embodiment of the antibody which specifically binds to the fusion protein of the invention, the antibody specifically binds either to epitopes formed by carboxylesterase residues within of the fusion protein. The antibody may however also bind to epitopes formed by the stretch of amino acids including the fusion point of the two heterologous polypeptides. This epitopes are characteristic (unique) for the fusion protein of the invention.

The antibody of the present invention can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. These antibodies can be used, for example, for the immunoprecipitation, affinity purification and immunolocalization of the polypeptides or fusion proteins of the invention as well as for the monitoring of the presence and amount of such polypeptides, for example, in cultures of recombinant prokaryotes or eukaryotic cells or organisms.

The antibody of the invention also includes embodiments such as chimeric, single chain and humanized antibodies, as well as antibody fragments, like, inter alia, Fab fragments. Antibody fragments or derivatives further comprise $F(ab')_2$, Fv or scFv fragments; see, for example, Harlow and Lane (1988) and (1999), loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of an polypeptide of the invention (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, amongst others, viruses or plasmid vectors.

The antibody described in the context of the invention is capable to specifically bind/interact with an epitope of the polypeptides or fusion protein of the invention. The term "specifically binding/interacting with" as used in accordance with the present invention means that the antibody does not or essentially does not cross-react with an epitope of similar structure. Thus, the antibody does not bind to prior art carboxylesterase of the present invention. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitope are considered specific for the epitope of interest and thus to be antibodies in accordance with this invention. Corresponding methods are described e.g. in Harlow and Lane, 1988 and 1999, loc cit.

The antibody specifically binds to/interacts with conformational or continuous epitopes which are unique for the polypeptides or fusion protein of the invention. A conformational or discontinuous epitope is characterized for polypeptide antigens by the presence of two or more discrete amino acid residues which are separated in the primary sequence, but come together on the surface of the molecule when the polypeptide folds into the native protein/antigen (Sela, (1969) Science 166, 1365 and Laver, (1990) Cell 61, 553-6). The two or more discrete amino acid residues contributing to the epitope are present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues which are present in a single linear segment of a polypeptide chain.

The present invention also relates to a primer which specifically hybridizes under stringent conditions to a polynucleotide of the present invention. Said primer is at least 10, more preferably at least 15, further preferably at least 20, furthermore preferably at least 25 nucleotides in length. The term "primer" when used in the present invention means a single-stranded nucleic acid molecule capable of annealing to the nucleic acid molecule of the present invention and thereby being capable of serving as a starting point for amplification or elongation. For an amplification reaction it is preferred that a pair of primers is elected. According to the present invention the term "pair of primers" means a pair of primers that are with respect to a complementary region of a nucleic acid molecule directed in the opposite direction towards each other to enable, for example, amplification by polymerase chain reaction (PCR).

The term "amplifying" refers to repeated copying of a specified sequence of nucleotides resulting in an increase in the amount of said specified sequence of nucleotides and allows the generation of a multitude of identical or essentially identical (i.e. at least 95% more preferred at least 98%, even more preferred at least 99% and most preferred at least 99.5% such as 99.9% identical) nucleic acid molecules or parts thereof. Such methods are well established in the art; see Sambrook et al. "Molecular Cloning, A Laboratory Manual", 2nd edition 1989, CSH Press, Cold Spring Harbor.

They include polymerase chain reaction (PCR™) and modifications thereof, ligase chain reaction (LCR™) to name some preferred amplification methods.

It is also preferred that the nucleic acid molecule of the invention is labelled. The label may, for example, be a radioactive label, such as $^{32}$P, $^{33}$P or $^{35}$S. In a preferred embodiment of the invention, the label is a non-radioactive label, for example, digoxigenin, biotin and fluorescence dye or a dye.

The present invention also relates to a composition comprising the polynucleotide of the present invention, the vector of the present invention, the host of the present invention, the polypeptide of the present invention, the antibody of the present invention and/or one or more primers of the present invention. The term "composition", as used in accordance with the present invention, relates to a composition which comprise at least one of the recited compounds. It may, optionally, comprises further molecules capable of altering the characteristics of the compounds of the invention thereby, for example, suppressing, stabilizing, blocking, modulating and/or activating their function. The composition may be in solid, liquid or gaseous form and may be, inter alia, in the form of (a) powder(s), (a) tablet(s), (a) solution(s) or (an) aerosol(s).

The present invention also relates to a method for the production of an optically active compound comprising allowing the enantioselective conversion of a racemic starting material by a polypeptide to the present invention. The term "optically active" as used herein describes the capability of a molecule to rotate the plane of polarization of a light wave. This capability is associated with asymmetry in the molecule. It is very often the result of a chiral centre. The term "enantioselective conversion" refers to the selective conversion of a chiral or prochiral substrate into an enantioenriched or enantiopure product.

Enzymatic conversions of optically active compounds are usually performed in a substrate concentration range between 1 and 100 mM, preferably between 1 and 20 mM and most preferably at a substrate concentration of 10 mM in a buffered medium most preferably sodium phosphate-buffer with a preferred concentration range of 5 to 100 mM, in particular 10 mM, most preferred 50 mM.

In a particularly preferred embodiment the reaction is carried out at a pH from 6.0 to 8.0, more preferred are 7.0 to 7.5 and most preferably at a pH of 7.5.

Preferably, in the context of the present invention, an optically active chiral compound has an optical purity of at least 70%, in particular more than 90% and at best >99%.

In a particular preferred embodiment, the reaction is carried out in a temperature range from 10 to 65° C., preferably 20 to 50° C., more preferably 34° C. to 39° C., most preferably at 37° C. In a preferred embodiment of the present invention the enzymatic activity may be from 1 to 20.000 µmol/min.

In a further preferred embodiment the reaction is carried out until a conversion of most preferably 50%, in particular 100% is reached.

In a preferred embodiment of the present invention, said optically active compound is (i) a secondary alcohol and the starting material is a racemic ester or an ester of a prochiral or meso-compound; (ii) a chiral carboxylic acid and the racemic starting material is a racemic ester; or (iii) a carboxylic acid ester and the racemic starting material is a racemic carboxylic acid.

In a more preferred embodiment of the present invention, said optical active secondary alcohol is (S)-1-phenyl-1-ethanol or (R)-1-phenyl-1-ethanol or (S)-1-phenyl-1-propanol or (R)-1-phenyl-1-propanol or (R)-1-phenyl-2-pentanol or (S)-1-phenyl-2-propanol or (R)-1-phenyl-2-propanol or (S)-1-phenyl-2-butanol or (R)-1-phenyl-2-butanol. The present invention also relates to a method for the production of an optically active chiral carboxylic acid comprising allowing the dynamic kinetic resolution of a racemic ester by a polypeptide of the present invention. Kinetic resolution limits the yield of each enantiomer to 50%. However, if the substrate racemizes quickly in the reaction mixture, then the yield of product enantiomer can be 100%. This resolution with in situ racemization is called dynamic kinetic resolution or asymmetric transformation of the second kind (for reviews see: Stecher and Faber, 1997; Ward, 1995; Faber, 2001; Pellissier, 2003; Schnell et al., 2003). The requirements for a dynamic kinetic resolution are: (1), the substrate must racemize at least as fast as the subsequent enzymatic reaction, (2), the product must not racemize, and (3), as in any asymmetric synthesis, the enzymic reaction must be highly stereoselective.

In a preferred embodiment of the present invention, said racemic starting material (educt) is produced by (a) a catalysis of a conversion by one or more different enzymes and/or the optically active compound (product) is the starting material (educt) for a further conversion by one or more different enzymes; or (b) a non-proteinaceous catalyst selected from the group consisting of oxidative agents used in organic synthesis by chemists. For instance, a peracid (e.g., m-Cl-per-benzoic acid) can be used to convert a ketone to an ester. More specifically, a cyclic ketone is converted to a lactone or an acyclic ketone is converted to an ester. Both products can serve as substrates for the esterases of the present invention. This Baeyer-Villiger oxidation may also be performed in a stereoselective manner using appropriate catalysts [47, 48]

Finally, in a more preferred embodiment of the present invention, said racemic starting material is produced by catalysis of a conversion by a Baeyer-Villiger monooxygenase [49]. A Baeyer-Villiger monooxygenase isolated from *Acinetobacter calcoaceticus* has been described in [50] and isolated from *Pseudomonas* sp. (*putida*) is known from [51].

THE FIGURES SHOW

FIG. 1 SEQ ID NO: 1 (Est1)
FIG. 2 SEQ ID NO: 2 (Est1)
FIG. 3 SEQ ID NO: 3 (Est5)
FIG. 4 SEQ ID NO: 4 (Est5):
FIG. 5 SEQ ID NO: 5 (Est7)
FIG. 6 SEQ ID NO: 6 (Est7):
FIG. 7 SEQ ID NO: 7 (Est8):
FIG. 8 SEQ ID NO: 8 (Est8):
FIG. 9 SEQ ID NO: 9 (Est56)
FIG. 10 SEQ ID NO: 10 (Est56):
FIG. 11 SEQ ID NO: 11 (Est63):
FIG. 12 SEQ ID NO: 12 (Est63):

The invention is illustrated by the following examples but it should be understood that this invention is not limited thereto or thereby.

EXAMPLE 1

Screening of Metagenomic Expression Libraries for New Esterases

*E. coli* DH12S cells harbouring recombinant pUC18 plasmids containing metagenomic DNA fragments in the range of 3-15 kbp were plated on tributyrin agar plates. These tributyrin agar plates were prepared as follows: 0.75 g of gum arab (Sigma) were dissolved in 7.5 ml of A. dest. to which 7.5 ml tributyrin (Sigma) were added. This mixture was added to 500 ml LB-agar containing 100 µg/ml ampicillin preheated to 50° C. and mixed using a blender or ultra-turrax device for 30 seconds. Afterwards the agar was poured into Petri dishes and allowed to solidify. The agar is characterised by a turbid appearance due to the insoluble tributyrin.

Cells plated on these tributyrin plates were incubated for 20-24 h at 37° C. and afterwards stored at RT. Plates were regularly inspected for the formation of halos around colonies which arise when the corresponding bacteria produce an active esterase. The hydrolysis of the tributyrin into butyric acid and glycerol leads to a clearing zone (halo) in the otherwise turbid agar because the reaction products are more soluble than the tributyrin itself.

Plasmids from clones that stand out by the formation of halos around the colony were isolated and retransformed to *E. coli* DH12S to verify to halo-forming phenotype. The identification of the genes encoding the enzymes responsible for the formation of the halo were identified by techniques known to persons in the state of the art.

EXAMPLE 2

Heterologous Expression of Metagenomic Esterases

In order to obtain enzyme samples of the esterases containing sufficient enzymatic activity for a characterisation of the enzyme either the metagenomic clone expressing the corresponding esterase or a more suited expression construct set up in a typical expression vector like e.g the pET26b-vector (Novagen) and a suitable expression host like e.g. *E. coli* Rosetta (DE3) (Novagen) were used. For the construction of the expression constructs, the corresponding esterase genes were PCR amplified to introduce unique restriction enzyme recognition sequences upstream and downstream of the open reading frame (ORF) which allowed to ligate the genes encoding the esterases with the expression vector e.g. pET26b in a definite way. The restriction enzyme recognition sequences were chosen on the basis of their absence in the coding region of the esterase gene and could be e.g. NdeI, HindIII, EcoRI, XhoI. The absence of unwanted second site mutations due to erroneous amplification by the polymerase was confirmed by sequencing of the cloned amplicon.

The metagenomic clones or the expression constructs were used to inoculate e.g. 200 ml of culture medium complemented with the appropriate antibiotic in a 1 l Erlenmayer flask. LB-medium and antibiotics in the following concentration were used: 100 µg/ml ampicillin, 25 µg/ml kanamycin, chloramphenicol 12.5 µg/ml. The initial optical density (O.D.$_{580}$) was adjusted to 0.05 and the cells grown at a temperature of 28° C. on a gyratory shaker. When the optical density reached the value of about 1 the expression from the lac-promoter of pUC18 or from the T7-promoter of vectors from the pET-vector series e.g. pET26 was induced by addition of IPTG in the concentration of 20 µM-500 µM. Cells were harvested 4 to 20 h after induction by centrifugation. The cell sediment was resuspended in 5 ml 5 mM Tris/HCl pH 8.0 and the cells disrupted by ultrasonication. In order to stabilize the enzyme preparations, glycerol was added in a final concentration of 50%.

EXAMPLE 3

Determination of Enzyme Activity

The hydrolytic activities of the enzyme samples were determined with p-nitrophenylbutyrate (pNPB) as substrate under the following conditions: 20 µl of enzyme preparation or dilutions of it were added to 80 µl of 5 mM Tris/HCl pH 8.0 in a 96 well microtiter plate. To start the reaction 100 µl of substrate solution were added. The substrate solution was prepared as follows: 3.4 µl of pNPB (Sigma) was dissolved in 1.2 ml isopropanol and mixed with 10.8 ml of 100 mM Tris/HCl pH 8.0, 20 mM CaCL$_2$ 2H$_2$O, 200 mM Triton X-100™. The increase of the extinction was followed at. 405 nm and RT for 10 min using a Spectramax 190 spectral photometer (Molecular Devices). The initial slope of the curve representing the enzymatic activity was calculated by using the software package Softmax Pro (Molecular Devices) and corrected for the value of a sample of an E. coli crude cell extract without a recombinant esterase. The activity "A" given as µmol×min$^{-1}$×ml$^{-1}$ was calculated with the formula:

$$A = \frac{\Delta E \times V_t}{\varepsilon \times d \times t \times V_{s \times} 1000}$$

where ΔE represents the change of extinction over the time "t" as given by the slope of the curve, Vt is the total volume of the reaction (200 µl), ε is the extinction coefficient of p-nitrophenolate (13000 M$^{-1}$×cm$^{-1}$), d is the path length and V$_s$ is the volume of the enzyme sample (20 µl).

EXAMPLE 4

Enzyme-Catalysed Kinetic Resolution of Chiral Esters

Preparative enzymatic conversions of racemic chiral esters were performed on a 10 ml scale with 0.25-0.3 mmol substrate and 1-2 ml enzyme preparation (50 U/ml based on p-nitrophenyl butyrate assay) in 50 mM phosphate-buffer pH 7.5. The reaction was stirred in a water bath at 37° C. up to a conversion of 50%. After addition of the same volume A. dest educts and/or products were extracted as follows: ethylesters were acidified with HCl (aq. 10%, 10 ml) and afterwards extracted with 4×20 ml diethylether. Methylesters were extracted first using a neutral to slight alkaline pH, afterwards the reaction was acidified to extract the reaction products. Acetylated substrates were extracted with 4×20 ml methylen chloride. In each case the organic phases were pooled, dried with Na$_2$SO$_4$ and afterwards evaporated. Reaction educts and products were separated by chromatography and analysed by NMR, polarimetric and GC-analysis to determine the grade of purity, the degree and sense of optical rotation and the enantiomeric excess.

EXAMPLE 5

Determination of Enantioselectivity by Chiral GC-Analysis

Acetates and alcohols were analysed by GC immediately after extraction with methylen chloride. Free acids were first converted to methylesters by use of an ethereal solution of diazomethane. After separation from residual diazomethane and organic solvents the methylesters were solved in 10 µl methylen chloride. The GC-analysis was performed on Shimadzu GC-14A gas chromatography device using the following chiral columns: Heptakis-(2,6-di-O-methyl-3-O-pentyl)-β-cyclodextrin or Heptakis-(2,3-di-O-acetyl-6-O-t.butyldimethylsilyl)-β-cyclodextri n. Retention times for the enantiomers of educts and products are given in table 7

TABLE 7

Retention times of the (S)- and (R)-enantiomers of the substrate esters and the corresponding products

| | retention time [min] | | | | |
|---|---|---|---|---|---|
| | educt | | product | | |
| Racemic compound | S | R | S | R | temperature |
| (R,S)-1-phenyl-2-pentylacetate (1) | 27.8 | 28.6 | 39.8 | 42.1 | 100° C. |
| (R,S)-1-phenyl-1-propylacetate (2) | 6.3 | 7.4 | 13 | 12.1 | 110° C. |
| (R,S)-1-phenyl-2-propylacetate (3) | 19.8 | 26.2 | 21.7 | 22.5 | 90° C. |
| (R,S)-1-phenyl-1-ethylacetate (4) | 4.5 | 5.9 | 7.4 | 6.7 | 110° C. |
| (R,S)-1-phenyl-3-butylacetate (5) | 15.9 | 23.5 | 17.6 | 18.5 | 110° C. |
| (R,S)-Tetrahydro-furan-2-yl-methylacetate (6) | 18.2 | 18.8 | / | / | 70° C. |
| (R,S)-Tetrahydro-furan-2-yl-ethylacetate (7) | 29.7 | 30.5 | 18.2 | 18.8 | 70° C. |

REFERENCES

[1] Bommarius A. S. & Riebel B. R., 2004, Biocatalysis, Wiley-VCH, Weinheim, Germany.
[2] Lorenz P. & Eck J., 2004, Screening for novel industrial biocatalysts, Engineering in Life Sciences, 4, 501-503.
[3] Schmid A. et al. 2001, Industrial biocatalysis today and tomorrow, Nature 409, 258-268.
[4] Ollis D. L. et al. 1992, The alpha/beta hydrolase fold, Protein Eng., 1992, 5, 197-211.
[5] Bornscheuer U., 2002, Microbial carboxyl esterases: classification, properties and application in biocatalysis, FEMS Microbiology Reviews, 26, 73-81.
[6] Arpigny J. L. & Jaeger K.-E., 1999, Bacterial lipolytic enzymes: classification and properties, Biochem J. 343, 177-183.
[7] Pleiss J., Fischer M., Peiker M., Thiele, C., & Schmid R. D., 2000, Lipase engineering database: understanding and exploiting sequence-structure-function relationships, J Mol Catal B, 10, 491-508.
[8] Henke E., Bornscheuer U. T., Schmid R. D. & Plaiss J., 2003, A molecular mechanisms of enantiorecognition of tertiary alcohols by craboxylesterases, Chem Bio Chem, 4, 485-493.

[9] Henke E., Pleiss J., Bornscheuer U. T., 2002, Activity of lipases and esterases towards tertiary alcohols: insights into structure-function relationships, Angew Chem Int Ed Engl., 41, 3211-3213.

[10] Wagner U. G., Petersen E. I., Schwab H., Kratky C., 2002, EstB from *Burkholderia gladioli*: a novel esterase with a beta-lactamase fold reveals steric factors to discriminate between esterolytic and beta-lactam cleaving activity, Protein Sci, 11, 467-478.

[11] Schlacher A., Stanzer T., Osprian I., Mischitz M., Klingsbichel E., Faber K., Schwab H., 1998, Detection of a new enzyme for stereoselective hydrolysis of linalyl acetate using simple plate assays for the characterization of cloned esterases from *Burkholderia gladioli*, J Biotechnol., 62, 47-54.

[12] Dröge M. J., Bos R., & Quax W. J., 2001, Paralogous gene analysis reveals a highly enantioselective 1,2-O-isopropylideneglycerol caprylate esterase of *Bacillus subtilis*, Eur. J. Biochem. 268, 3332-3338.

[13] Brogden et al., Drugs, 18, 241-277 (1979).

[14] D. Barettino et al., Improved method for PCR-site directed mutagensis, 1994, Nucleic Acids Res, 22, 541-542

[15] A. Urban et al. A rapid and efficient method for site-directed mutagenesis using one-step overlap extension PCR, 1997, Nucleic Acids Res, 25, 2227-2228

[16] A. Seyfang & J. H. Jin, Multiple site-directed mutagenesis of more than 10 sites simultaneously and in a single round, 2004, Anal Biochem, 324, 285-291

[17] W. R. Pearson and D. J. Lipman, Improved Tools for Biological Sequence Comparison, 1988, Proc. Natl. Acad. Sci., USA 85; 2444-2448

[18] D. A. Benson, I. K. Mizrachi, D. J. Lipman, J. Ostell, D. L. Wheeler, GenBank, 2005, Nucleic Acids Res. 33, D34-D38

[19] Kostichka, K., Thomas, S. M., Gibson, K. J., Nagarajan, V. and Cheng, Q. Cloning and characterization of a gene cluster for cyclododecanone oxidation in *Rhodococcus ruber* SC1, J. Bacteriol. 183, 6478-6486 (2001).

[20] Nierman, W. C. et al. Genomic sequence of the pathogenic and allergenic filamentous fungus *Aspergillus fumigatus*, Nature 438, 1151-1156 (2005).

[21] Kim, Y. J., Choi, G. S., Kim, S. B., Yoon, G. S., Kim, Y. S. and Ryu, Y. W. Screening and characterization of a novel esterase from a metagenomic library, Protein Expr. Purif. 45, 315-323 (2006).

[22] Wei, Y. et al. Crystal structure of brefeldin A esterase, a bacterial homolog of the mammalian hormone-sensitive lipase, Nat. Struct. Biol. 6, 340-345 (1999).

[23] Rashamuse, K. J., Burton, S. G., Stafford, W. H. and Cowan, D. A., "Molecular characterization of a novel family VIII esterase from *Burkholderia multivorans* UWC10;" J. Mol. Microbiol. Biotechnol. 13(1-3), 181-188 (2007).

[24] Woods, D. E. and Nierman, W.C.; *Burkholderia pseudomallei* 1710b chromosome II, complete sequence, Accession No. CP000125 AAHT01000000AAHT01000001-AAHT01000077.

[25] Lee, S. W., Won, K., Lim, H. K., Kim, J. C., Choi, G. J. and Cho, K. Y., Screening for novel lipolytic enzymes from uncultured soil microorganisms, Appl. Microbiol. Biotechnol. 65 (6), 720-726 (2004).

[26] Kim, H. S., Schell, M. A., Yu, Y., Ulrich, R. L., Sarria, S. H., Nierman, W. C. and Deshazer, D., Bacterial genome adaptation to niches: Divergence of the potential, virulence genes in three *Burkholderia* species of different survival strategies, BMC Genomics 6 (1), 174 (2005).

[27] Nierman, W. C. et al. Structural flexibility in the *Burkholderia mallei* genome, Proc. Natl. Acad. Sci. U.S.A. 101, 14247-14251 (2004).

[28] Ueda, K. et al. Genome sequence of *Symbiobacterium thermophilum*, an uncultivable bacterium that depends on microbial commensalism, Nucleic Acids Res. 32 (16), 4937-4944 (2004).

[29] Copeland, A., Lucas, S., Lapidus, A., Barry, K., Defter, J.C., Glavina, T., Hammon, N., Israni, S., Pitluck, S., Goltsman, E., Martinez, M., Schmutz, J., Larimer, F., Land, M., Lykidis, A., and Richardson, P., *Rallstonia eutropha* JMP134 chromosome 2, complete sequence Accession No. CP000091.1.

[30] Musidlowska, A., Lange S., Bornscheuer U. T., 2001, By Overexpression in the Yeast *Pichia pastoris* to Enhanced Enantioselectivity: New Aspects in the Application of Pig Liver Esterase, Angew Chem Int Ed Engl., 40, 2851-2853.

[31] Musidlowska-Persson A, Bornscheuer U T, 2003, Site directed mutagenesis of recombinant pig liver esterase yields mutants with altered enantioselectivity, Tetrahedron: Assymetry 14, 1341-1344.

[32] Chen C. S., Fujimoto Y, Girdaukas G., Sih C. J., 1987, Quantitative analyses of the biochemical kinetic resolutions of enantiomers, J. Am. Chem. Soc., 104, 7294-7299.

[33] Chen C. S., Wu S., Girdaukas G., Sih C. J., 1987, Quantitative analyses of the biochemical kinetic resolutions of enantiomers 2: Enzyme catalysed esterification in water-organic solvents biphasic systems, J. Am. Chem. Soc., 109, 2812-2817.

[34] Musidlowska-Persson A, Bornscheuer U T, 2002, Substrate specificity of the γ-isoenzyme of recombinant pig liver esterase towards acetates of secondary alcohols, J. Mol. Catal. B, 19-20, 129-133.

[35] Dissertation Rüggeberg, 2001, Beiträge zur gerichteten Evolution von Enzymen für die organische Synthese, Ruhr-Universität Bochum

[36] For review, see: Boivin, T. L. B. *Tetrahedron* 1987, 43, 3309 and references therein. (b) Barrett, A. G. M.; Sheth, H. G. *J. Org. Chem.* 1983, 48, 5017. (c) Rao, Y. S. *Chem. Rev.* 1976, 76, 625. (d) Pattenden, G. *Prog. Chem. Nat. Prod.* 1978, 35, 133. (e) Knight, D. W. *Contemp. Org. Synth.* 1994, 1, 287. (f) Gerlach, H.; Wetter, H. *Helv. Chim. Acta* 1974, 57, 2306. (g) Schmidt, U.; Gombos, J.; Haslinger, E.; Zak, H. *Chem. Ber.* 1976, 109, 2628. (h) Bartlett, P. A.; Meadows, J. D.; Ottow, E. *J. Am. Chem. Soc.* 1984, 106, 5304. (i) Bryson, T. A. *J. Org. Chem.* 1973, 38, 3428. (j) Yamaguchi, M.; Hirao, I. *Chem. Lett.* 1985, 337. (k) Lygo, B. *Tetrahedron* 1988, 44, 6889.

[37] For information about tetronasin, see: Boons, G.-J.; Clase, J. A.; Lennon, I. C.; Ley, S. V.; Staunton, J. *Tetrahedron* 1995, 51, 5417 and references therein.

[38] For information about tetronomycin, see: Iqbal, J.; Pandey, A.; Chauhan, B. P. S. *Tetrahedron* 1991, 47, 4143.

[39] Booth, P. M.; Fox, C. M. J.; Ley, S. V. *J. Chem. Soc., Perkin Trans.* 1 1987, 121.

[40] Marvell, E. N.; Titterington, D. *Tetrahedron Lett.* 1980, 2123. (b) Tsuji, J.; Kobayashi, Y.; Kataoka, H.; Takahashi, T. *Tetrahedron Lett.* 1980, 1475.

[41] Wang, T.; Chen, J.; Landrey, D. W.; Zhao, K. *Synlett* 1995, 543.

[42] For carbohydrate derived bicyclic 2-alkylidenetetrahydrofurans, see: (a) Al-Tel, T. H.; Voelter, W. *J. Chem. Soc., Chem. Commun.* 1995, 239. (b) Al-Tel, T. H.; Meisenbach, M.; Voelter, W. *Liebigs Ann.* 1995, 689.

[43] Arai, H.; Miyajima, H.; Mushiroda, T.; Yamamoto, Y. *Chem. Pharm. Bull.* 1989, 12, 3229.

[44] Mori, K.; Sasaki, M.; Tamada, S.; Suguro, T.; Masuda, S. *Tetrahedron* 1979, 35, 1601.

[45] Römpp Lexikon Naturstoffe (Eds.: W. Steglich, B. Fugmann, S. Lang-Fugmann), Thieme, Stuttgart, 1997.

[46] For furan natural products, see references 1-11 cited in: T. Bach, L. Krüger, *Eur. J. Org. Chem.* 1999, 2045.

[47] C. Bolm, G. Schlingloff, K. Weickhardt, Angew. Chem. Int. Ed. Engl. 1994, 33, 1848-1849.

[48] G. Strukul, Angew. Chem., Int. Ed. 1998, 37, 1199-1209

[49] Mihovilovic M D, Müller B, Stanetty P (2002) Monooxygenase-mediated Baeyer-Villiger Oxidations. Eur J Org Chem 3711-3730

[50] R. Gagnon, et al. J. Chem. Soc., Perkin Trans. 1 1994, 2537-2543.
J. D. Stewart, K. W. Reed, J. Zhu, G. Chen, M. M. Kayser, J. Org. Chem. 1996, 61, 7652-7653.
J. D. Stewart et al. J. Am. Chem. Soc. 1998, 120, 3541-3548; M. Kayser, G. Chen, J. Stewart, Synlett. 1999, 1, 153-158.
M. D. Mihovilovic et al. J. Mol. Catal. B: Enzym. 2001, 11, 349-353.

[51] G. Grogan et al. Willetts, Biotechnol. Lett. 1993, 15, 913-918. G. Grogan et al. J. Gen. Microbiol. 1993, 139, 797-805; D. G. Taylor, P. W. Trudgill, J. Bacteriol. 1986, 165, 489-497.

The invention claimed is:

1. An isolated or purified polynucleotide encoding an enzyme having carboxylesterase [E.C. 3.1.1.1] activity, wherein the polynucleotide is fused to a heterologous promoter and wherein the polynucleotide is selected from the group consisting of
   (a) a polynucleotide encoding an amino acid sequence as set forth SEQ ID NO:10;
   (b) a polynucleotide comprising a nucleotide sequence set forth in SEQ ID NO:9;
   (c) a polynucleotide comprising a nucleotide sequence encoding a fragment of an enzyme encoded by a polynucleotide of (a) or (b), and wherein said fragment has a Sm-Xaa-Ser-Xaa-Gly (SEQ ID NO:13) motif, a catalytic triad composed of amino acids Ser-Glu-His or Ser-Asp-His, and a GGGX (SEQ ID NO:15) motif;
   (d) a polynucleotide at least 70% identical to a polynucleotide encoding an enzyme as set forth in one of SEQ ID NO:10, wherein the enzyme has a Sm-Xaa-Ser-Xaa-Gly (SEQ ID NO:13) motif, a catalytic triad composed of amino acids Ser-Glu-His or Ser-Asp-His, and a GGGX (SEQ ID NO:15) motif; and
   (e) a polynucleotide comprising a nucleotide sequence degenerate to the polynucleotide of (d).

2. The polynucleotide according to claim 1, wherein the coding region is fused with a heterologous or homologous polynucleotide.

3. The polynucleotide of claim 2, wherein said heterologous or homologous polynucleotide encodes a polypeptide.

4. A vector containing the polynucleotide of any one of claims 1 to 3.

5. A host genetically engineered with the polynucleotide of any one of claims 1 to 3.

6. The host according to claim 5 which is a prokaryotic host selected from the group consisting of *E. coli*, *Bacillus* sp., *Pseudomonas* sp., *Streptomyces* sp., *Mycobacterium* sp., *Caulobacter* sp., *Rhodobacter* sp., *Lactococcus* sp., *Burkholderi* sp. and *Ralstonia* sp.

7. The host according to claim 5, wherein said host expresses (a) the polypeptide encoded by the polynucleotide of claim 1 and (b) one or more additional enzyme(s) wherein said enzymes in toto catalyze a multi-step conversion of a substrate or contribute thereto.

8. The host according to claim 7, wherein the one or more additional enzyme(s) is/are a Baeyer-Villiger monooxygenase and, optionally, an enzyme for the regeneration of the cofactor NAD(P)H.

9. A process for producing a polypeptide having carboxylesterase [E.C. 3.1.1.1] activity, comprising culturing the host of claim 5 and recovering the polypeptide produced by said host.

10. An isolated or purified labelled primer, having a radioactive label or a non-radioactive label, wherein the labelled primer specifically hybridizes under stringent conditions of incubation at 42 deg C. in a solution comprising 50% formamide, 5×SSC (750 mM NaCl, 75 mM sodium citrate), 50 mM sodium phosphate (pH 7.6), 5×Denhardt's solution, 10% dextran sulfate and 20 ug/ml denatured, sheared salmon sperm DNA, followed by washing in 0.1×SSC at about 65 deg C to a polynucleotide of any one of claims 1 to 3.

11. A composition comprising the polynucleotide of any one of claims 1 to 3.

12. The polynucleotide of claim 1, wherein the polynucleotide is at least 95% identical to a polynucleotide encoding an enzyme as set forth in SEQ ID NO:10.

13. The polynucleotide of claim 1, wherein the polynucleotide is at least 80% identical to a polynucleotide encoding an enzyme as set forth in SEQ ID NO:10.

14. The polynucleotide of claim 1, wherein the polynucleotide is at least 85% identical to a polynucleotide encoding an enzyme as set forth in SEQ ID NO:10.

15. The polynucleotide of claim 1, wherein the polynucleotide is at least 90% identical to a polynucleotide encoding an enzyme as set forth in SEQ ID NO:10.

16. The labelled primer of claim 10, wherein the label is a radioactive label.

17. The labelled primer of claim 10, wherein the label is a non-radioactive label.

18. The labelled primer of claim 17, wherein the non-radioactive label is a dye.

\* \* \* \* \*